United States Patent
Burke et al.

(10) Patent No.: US 11,045,287 B2
(45) Date of Patent: Jun. 29, 2021

(54) DENTISTRY TOOL

(71) Applicant: NOBEL BIOCARE SERVICES AG, Kloten (CH)

(72) Inventors: Edmund Burke, Niederbuchsiten (CH); David Sollberger, Glattpark (CH); Silvio Nussbaumer, Zurich (CH); Stefan Holst, Kusnacht (CH); Hans Geiselhoringer, Kloten (CH); Antony Quarry, Caslano (CH); Jorg Weitzel, Rielasingen-Worblingen (DE)

(73) Assignee: NOBEL BIOCARE SERVICES AG, Kloten (CH)

( * ) Notice: Subject to any disclaimer, the term of this patent is extended or adjusted under 35 U.S.C. 154(b) by 0 days.

(21) Appl. No.: 16/073,281

(22) PCT Filed: Jan. 30, 2017

(86) PCT No.: PCT/EP2017/051956
§ 371 (c)(1),
(2) Date: Jul. 26, 2018

(87) PCT Pub. No.: WO2017/129828
PCT Pub. Date: Aug. 3, 2017

(65) Prior Publication Data
US 2019/0038385 A1     Feb. 7, 2019

(30) Foreign Application Priority Data
Jan. 29, 2016   (EP) ..................................... 16153496

(51) Int. Cl.
*A61C 8/00*     (2006.01)
*A61B 17/16*    (2006.01)

(52) U.S. Cl.
CPC ........ *A61C 8/0089* (2013.01); *A61B 17/1615* (2013.01); *A61B 17/1655* (2013.01); *A61B 17/1673* (2013.01)

(58) Field of Classification Search
CPC ..... A61C 8/0089; A61C 3/02; A61B 17/1615; A61B 17/1655; A61B 17/1673;
(Continued)

(56) References Cited

U.S. PATENT DOCUMENTS

| 4,594,034 A | 6/1986 | Maier |
| 4,765,419 A | 8/1988 | Scholz et al. |

(Continued)

FOREIGN PATENT DOCUMENTS

| CH | 410276 | 10/1966 |
| CN | 103249372 A | 8/2013 |

(Continued)

OTHER PUBLICATIONS

International Search Report for Application No. PCT/EP2017/051956 dated Apr. 7, 2017 in 2 pages [the ISR for the PCT Application of this US national phase application].

(Continued)

*Primary Examiner* — Heidi M Eide
(74) *Attorney, Agent, or Firm* — Knobbe, Martens, Olson & Bear, LLP

(57) ABSTRACT

A drill bit and method for normalizing bone is provided. The drill bit has a non-round drill bit core that is adapted to cut hard bone and to not cut soft bone. The drill bit has a cutting edge which may be positioned within a compression zone of the non-round drill bit core. The rotational speed of the drill bit and the profile of the drill bit core are tuned so that hard bone recovers into a cutting zone defined by the cutting edge while soft bone remains outside of the cutting zone. The (Continued)

insertion torque of the drill bit can be measured to determine when the normalization is adequate.

16 Claims, 15 Drawing Sheets

(58) Field of Classification Search
CPC ... A61B 17/1662–1688; Y10T 408/904; Y10T 408/9042; Y10T 408/9046; Y10T 408/9097; B23B 2251/12; B23B 2251/241; B23B 2251/245; B23B 2251/40; B23B 2251/408
USPC ............... 408/113–114, 222, 215, 219, 220; 433/165–166; 470/198, 199, 204
See application file for complete search history.

(56) References Cited

U.S. PATENT DOCUMENTS

| | | | |
|---|---|---|---|
| 5,007,835 A * | 4/1991 | Valen | A61C 8/0022 433/174 |
| 5,087,201 A | 2/1992 | Mondani et al. | |
| 5,261,818 A | 11/1993 | Shaw | |
| 5,437,675 A | 8/1995 | Wilson | |
| 5,857,995 A * | 1/1999 | Thomas | A61B 17/1615 604/22 |
| 5,947,659 A | 9/1999 | Mays | |
| 6,042,376 A | 3/2000 | Cohen et al. | |
| 6,171,312 B1 | 1/2001 | Beaty | |
| 6,179,616 B1 | 1/2001 | Danger | |
| 6,189,616 B1 | 2/2001 | Gano et al. | |
| 6,217,267 B1 * | 4/2001 | Sugano | B23G 7/02 408/220 |
| 6,734,858 B2 | 5/2004 | Attar et al. | |
| 6,761,697 B2 | 7/2004 | Rubinstenn et al. | |
| 6,942,484 B2 | 9/2005 | Scianamblo | |
| 7,094,056 B2 | 8/2006 | Scianamblo | |
| 7,147,469 B2 | 12/2006 | Garman | |
| 7,220,254 B2 | 5/2007 | Altshuler et al. | |
| 7,300,281 B2 | 11/2007 | Cantatore et al. | |
| 7,357,606 B1 | 4/2008 | Pettit et al. | |
| 7,402,040 B2 | 7/2008 | Turri | |
| 7,967,605 B2 | 6/2011 | Goodis | |
| 8,094,186 B2 | 1/2012 | Fukuoka et al. | |
| 8,496,476 B2 | 7/2013 | Scianamblo | |
| 9,022,783 B2 | 5/2015 | Huwais | |
| 9,028,253 B2 | 5/2015 | Huwais | |
| 9,138,819 B2 * | 9/2015 | Ohhashi | B23G 5/20 |
| 9,179,923 B2 | 11/2015 | Gubellini | |
| 9,271,740 B2 | 3/2016 | Scianamblo | |
| 9,277,925 B2 | 3/2016 | Scianamblo | |
| 9,326,778 B2 | 5/2016 | Huwais | |
| 9,526,593 B2 | 12/2016 | Huwais | |
| 9,737,312 B2 | 8/2017 | Huwais | |
| 10,039,621 B2 | 8/2018 | Huwais | |
| 10,568,639 B2 | 2/2020 | Huwais | |
| 2002/0119418 A1 | 8/2002 | Matsutani et al. | |
| 2002/0173794 A1 | 11/2002 | Happonen et al. | |
| 2003/0022132 A1 | 1/2003 | Jesch | |
| 2003/0077553 A1 | 4/2003 | Brock et al. | |
| 2003/0143057 A1 | 7/2003 | Shinjo | |
| 2004/0191723 A1 | 9/2004 | Shearer et al. | |
| 2004/0258492 A1 * | 12/2004 | Hakansson | B23G 7/02 408/222 |
| 2005/0266375 A1 | 12/2005 | Brock et al. | |
| 2007/0101827 A1 | 5/2007 | Quan et al. | |
| 2008/0080951 A1 | 4/2008 | Lin | |
| 2012/0191103 A1 | 7/2012 | Joerneus et al. | |
| 2013/0004918 A1 | 1/2013 | Huwais | |
| 2013/0170920 A1 | 7/2013 | Ogawa | |
| 2015/0056032 A1 | 2/2015 | Scianamblo | |
| 2016/0135920 A1 | 5/2016 | Jorneus | |
| 2016/0278880 A1 | 9/2016 | Scianamblo | |

FOREIGN PATENT DOCUMENTS

| | | |
|---|---|---|
| CN | 103717175 A | 4/2014 |
| CN | 204121189 U | 1/2015 |
| DE | 43 16 955 | 5/1994 |
| DE | 197 32 983 | 2/1999 |
| EP | 1 184 004 | 3/2002 |
| EP | 1 478 301 | 11/2004 |
| EP | 1 236 441 | 9/2006 |
| EP | 1 531 752 | 12/2009 |
| EP | 1 624 825 | 12/2009 |
| EP | 2 292 175 | 3/2011 |
| EP | 3 035 871 | 5/2019 |
| JP | S57-127608 | 8/1982 |
| JP | 11-019825 A | 1/1999 |
| JP | 2007-292131 | 11/2007 |
| RU | 2515400 | 5/2014 |
| UA | 18573 | 12/1997 |
| WO | WO 2001/085051 | 11/2001 |
| WO | WO 2011/087200 | 7/2011 |
| WO | WO 2014/076653 | 5/2014 |

OTHER PUBLICATIONS

European Search Report dated Aug. 7, 2016 for Application No. EP 16 15 3496; 2 pages.
Brochure, "Soft Dilating System; New Technique for the preparation of the implant bed," Arsline S.A; https://web.archive.org/web/20171015000000*/http://www.arsline.com/pdf/sds.brocureEN.pdf;. indicated as being available as early as Mar. 3, 2017 by Internet Archive Way Back Machine.
European Search Report for European Patent Application No. EP16 15 3496, dated Jul. 8, 2016 in 2 pages.
Oct. 29, 2018, Office Action for Japanese Application No. 2018-530897.

* cited by examiner

US 11,045,287 B2

DENTISTRY TOOL

CROSS-REFERENCE TO RELATED APPLICATIONS

This application is a national stage application under 35 U.S.C. § 371 of International Application No. PCT/EP2017/051956, filed on Jan. 30, 2017, which published in English as WO 2017/129828 A1 on Aug. 3, 2017, and which claims priority benefit of EP Patent Application No. 16153496.1, filed on Jan. 29, 2016.

FIELD

The present disclosure relates generally to a drill bit that can be used in surgery and, in certain embodiments, to drill bits used in dental surgery or to a tool to enlarge an osteotomy.

DESCRIPTION OF THE RELATED ART

Holes are often formed in the jaw bones of patients in various circumstances and implantation situations. It is known that proper preparation of an implant-receiving hole can be important to achieving osseointegration and long-term success of the dental implant. Given that the density, orientation and quality of bone can differ from patient to patient, it is often necessary to use multiple tools and/or to have different drilling protocols available to prepare the implant-receiving hole according to the density, orientation and quality of the patient's jawbone. For example, depending upon the density of the bone at the implantation site, a different set of tools and/or drill protocols can be used to remove high-density bone from the hole as compared to an implantation site with low-density bone.

SUMMARY

The systems, methods and devices described herein have innovative aspects, no single one of which is indispensable or solely responsible for their desirable attributes. Without limiting the scope of the claims, some of the advantageous features will now be summarized.

One aspect of the disclosure herein is the recognition that there is a need to simplify and improve the hole formation function so that fewer drilling stages and/or protocols are needed and so that the result of the hole formation is still satisfactory. Another aspect of the disclosure herein is the recognition that it would be advantageous the number of instruments and drills can be reduced without compromising the precision of the hole formation across a range of bone quality, density and/or orientation situations.

In a first aspect, an object of the invention is a drill bit comprising:
an apical end, a coronal end, and a longitudinal axis extending between the apical end and the coronal end;
a drill bit core circumferentially surrounding the longitudinal axis and having at least a portion with a non-round or non-circular profile when viewed in a plane perpendicular to the longitudinal axis, the portion with a non-round or non-circular profile forming at least one first compression zone;
a first cutting edge; and
a guide thread which extends radially outward from the drill bit core.

The first cutting edge may be disposed within the first compression zone of the drill bit core.

The first cutting edge may be a first radial distance from the longitudinal axis and a maximum outer dimension of the drill bit core may be a second radial distance from the longitudinal axis. The second radial distance may be larger than the first radial distance. The extremity of the first radial distance may be different than the extremity of the second radial distance. The extremity of the first radial distance may be at a different angular position than the extremity of the second radial distance. In other words, the first cutting edge may be at a different angular position than a maximum outer dimension of the drill bit core.

In a second aspect, an object of the invention is a drill bit comprising:
an apical end, a coronal end, and a longitudinal axis extending between the apical end and the coronal end;
a drill bit core circumferentially surrounding the longitudinal axis and having at least a portion with a non-round or non-circular profile when viewed in a plane perpendicular to the longitudinal axis, the portion with a non-round or non-circular profile forming at least one first compression zone; and
a first cutting edge disposed within the first compression zone of the drill bit core,
wherein the first cutting edge is a first radial distance from the longitudinal axis and a maximum outer dimension of the drill bit core is a second radial distance from the longitudinal axis, the second radial distance being larger than the first radial distance.

The drill bit may further comprise a guide thread which extends radially outward from the drill bit core.

The drill bit according to the invention can comprise the following features taken alone or in combination:
the drill bit core is oval-shaped;
the drill bit core tapers toward the apical end;
the drill bit core comprises a maximum outer dimension that circumferentially shifts about the longitudinal axis as the drill bit core extends toward the apical end;
the non-round or non-circular profile is tri-lobed or tri-oval;
the drill bit core further comprises a second cutting edge disposed within a second compression zone;
the drill bit core further comprises a cutting flute;
the cutting flute wraps circumferentially around the longitudinal axis as the cutting flute extends between the apical end and the coronal end of the drill bit; the cutting flute may start at the coronal end of the drill bit; the cutting flute may not extend to the apical end of the drill bit; the cutting flute may not be present in at least a portion, e.g., in at least the most apical portion, of the apical end of the drill bit; the cutting flute may not be present at the entire apical end of the drill bit; the first cutting edge is a first radial distance from the longitudinal axis and a maximum outer dimension of the drill bit core is a second radial distance from the longitudinal axis, the drill bit core having a no-cutting zone defined as the difference between the second radial distance and the first radial distance;
the no-cutting zone remains constant between the apical and coronal ends of the drill bit.

The guide thread may have a height that is defined as the distance the guide thread extends radially away from the drill bit core. The height of the guide thread may be in the range of between 0 and 1000 µm, between 0 and 500 µm, or between 50 and 250 µm. In particular, the height of the guide thread may be 300 µm.

The guide thread may have a width of 250 µm or less, 200 µm or less, or 150 µm or less.

The guide thread may have a pitch of 1 mm or less.
The guide thread may have a substantially round profile, e.g., a substantially circular profile, when viewed in a plane perpendicular to the longitudinal axis.

The width of the guide thread may be different from the width of the cutting flute. The height of the guide thread may be different from the height of the cutting flute. The pitch of the guide thread may be different from the pitch of the cutting flute.

The cutting flute may have an opening with an angular length in the range of between 50° and 70°. The angular length of the opening of the cutting flute may be 60°.

In a third aspect, an object of the invention is a method of preparing an osteotomy, the method comprising:

drilling a hole in a jaw bone with a non-round or non-circular drill bit.

The method can further comprise the following steps taken alone or in combination:

measuring an insertion torque of the drill bit during the drilling step.

evaluating whether the insertion torque is within an acceptable range.

stopping the drilling if the insertion torque is within an acceptable range; and using a second drill bit to modify the hole and repeating the measuring and evaluating step.

In a fourth aspect, an object of the invention is a method of implanting an implant into a jaw bone comprising:

drilling a hole in a jaw bone with a non-round or non-circular drill bit; and implanting an implant into the hole.

The method can further comprise the following steps of:

measuring an insertion torque of the drill bit during the drilling step;

evaluating whether the insertion torque is within an acceptable range;

installing an implant if the insertion torque is within an acceptable range; and modifying the hole and repeating the measuring and evaluating step if the insertion torque is not within an acceptable range.

In a fifth aspect, an object of the invention is a kit of parts comprising a drill bit of the first aspect or the second aspect and an implant, in particular a dental implant.

The implant may comprise a thread. The drill bit may comprise a guide thread which extends radially outward from the drill bit core. The guide thread may differ from the thread of the implant in pitch and/or height and/or width.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
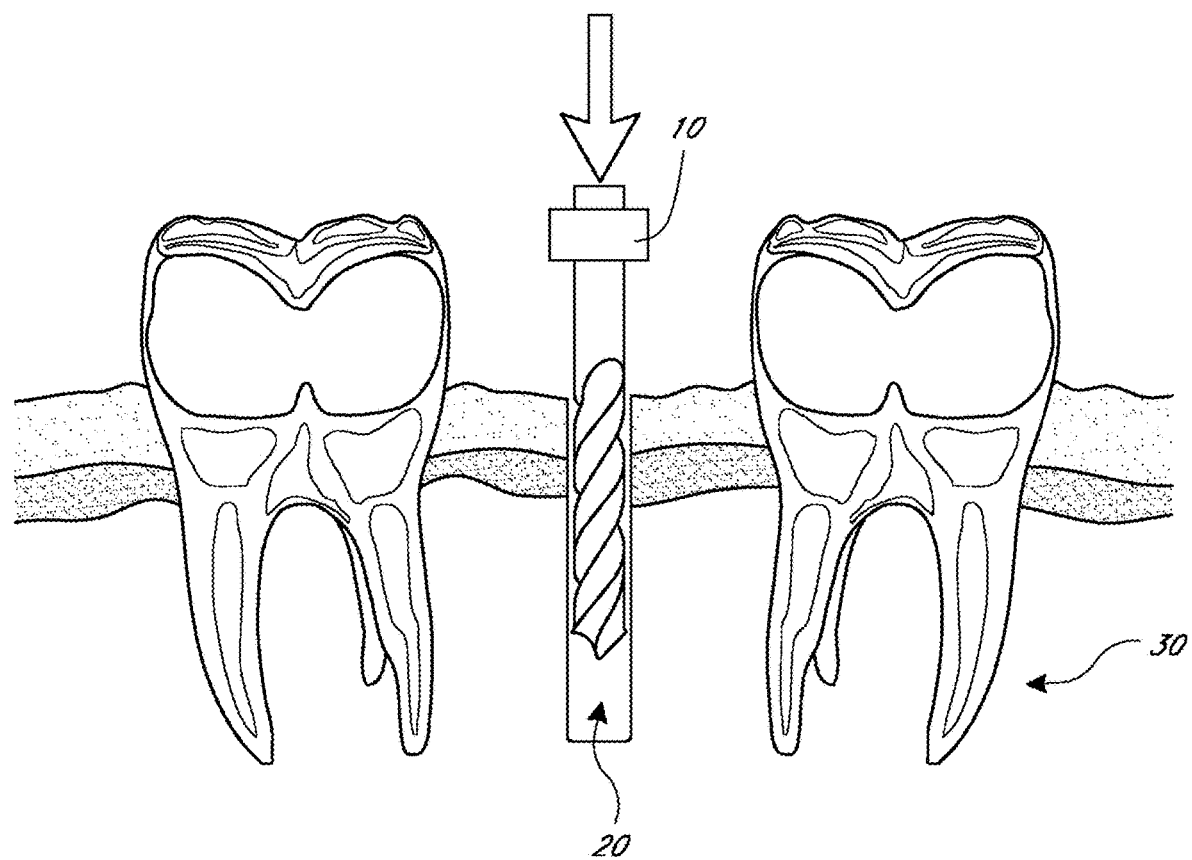
FIG. 1 shows an implant-receiving hole being prepared in a jaw bone.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

FIG. 1 depicts an example traditional dental drill bit 10 drilling a hole 20 into a jaw bone 30 in order to prepare the jaw bone 30 for receiving a dental implant. Long-term success of a dental implant can depend on proper preparation of the implant site. For example, the torque required to advance the implant into the jaw bone 30 (also referred to as "insertion torque") can serve as an indication of initial stability of the implant. Implant stability can be an important factor for implant osseointegration and immediate loading. Given that the jaw bone 30 can consist of different bone types and/or each patient may have a jawbone of different quality, orientation and/or density, the method of preparing the jaw bone 30 to receive an implant may need to be tailored according to the density, orientation and/or quality of the bone at the site of implantation. For example, failure to remove a sufficient amount of bone from an implant site having high-density bone can result in a high insertion torque, which can harm the surrounding bone. Removing too much bone from an implant site having low-density bone can result in a low insertion torque, which can be indicative that implant micro-motion will frustrate osseointegration.

Figure 2:
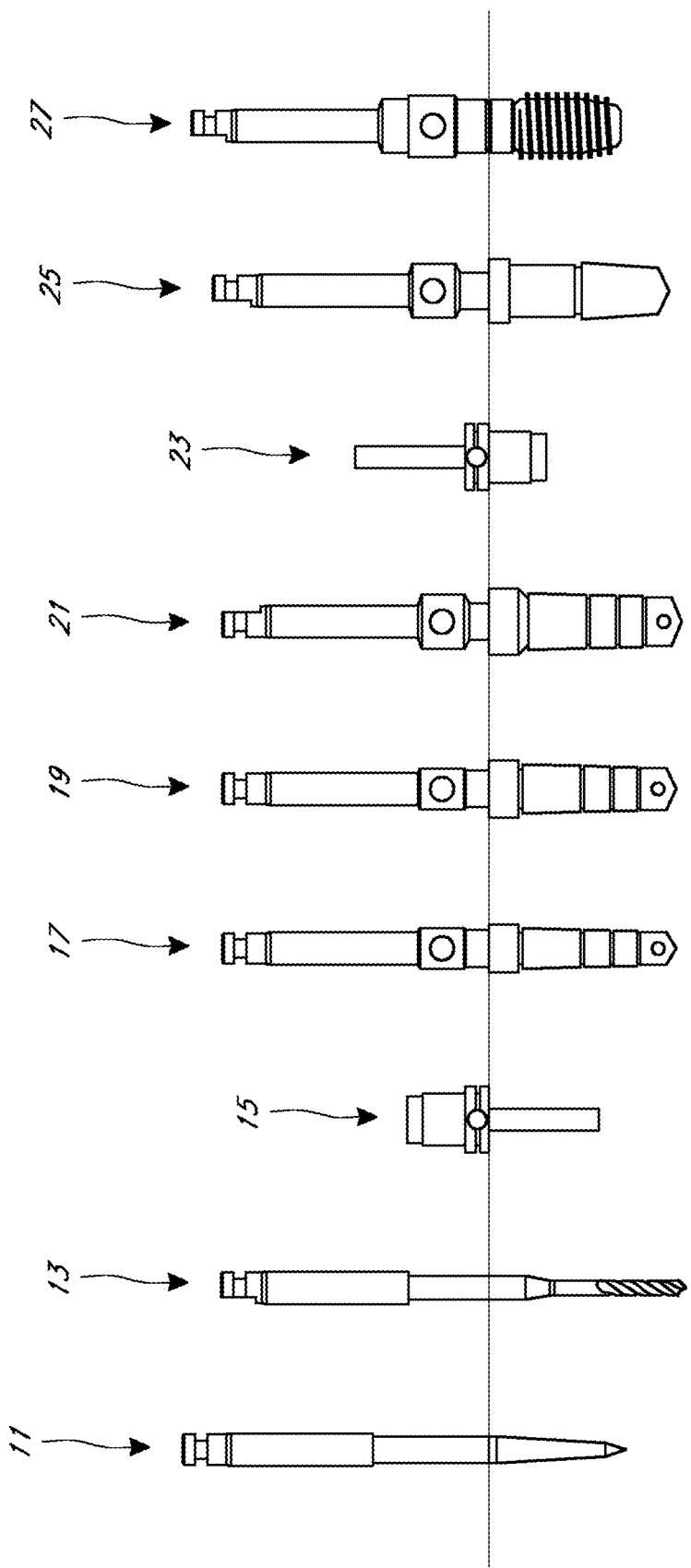
FIG. 2 shows a panel of tools that can be used to prepare a hole in a jaw bone.

FIG. 2 illustrates a traditional method of preparing the jaw bone 30 to receive a dental implant that employs relatively complex drill protocols with multiple steps and decisions, especially for dense bone situations. For example, a dense bone drilling protocol may include up to seven drills and taps, including: a precision drill 11, a 2-mm-diameter tapered drill 13, a first direction indicator 15, a 3.5-mm-diameter tapered drill 17, a 4.3-mm-diameter tapered drill 19, a 5.0-mm-diameter tapered drill 21, a second direction indicator 23, a 5.0-mm-diameter dense bone drill 25, and a 5.0-mm-diameter screw tap tapered drill 27. Dental implant manufacturers provide guidelines on which combination of tools to use, in which bone quality situations, to achieve the desired insertion torques. In some situation, a clinician must first estimate local bone quality before choosing which drill protocol to follow. If the estimation of bone quality is incorrect, the chosen drill protocol may also be incorrect, which can lead to an insertion torque that is too high or too low.

One aspect of the present disclosure is the recognition that in regions having low-density bone, insertion torques can be improved by leaving the low-density bone in place. Moreover, in regions of high-density bone, it can be desired to remove the high-density bone from the site of implantation in order to make room for the incoming implant. Accordingly, it would be advantageous to have an instrument and/or method that can selectively cut away high-density bone from the implant site while leaving low-density bone in place. Such an instrument and/or method may also advantageously simplify drill protocol procedures.

Figure 3A:
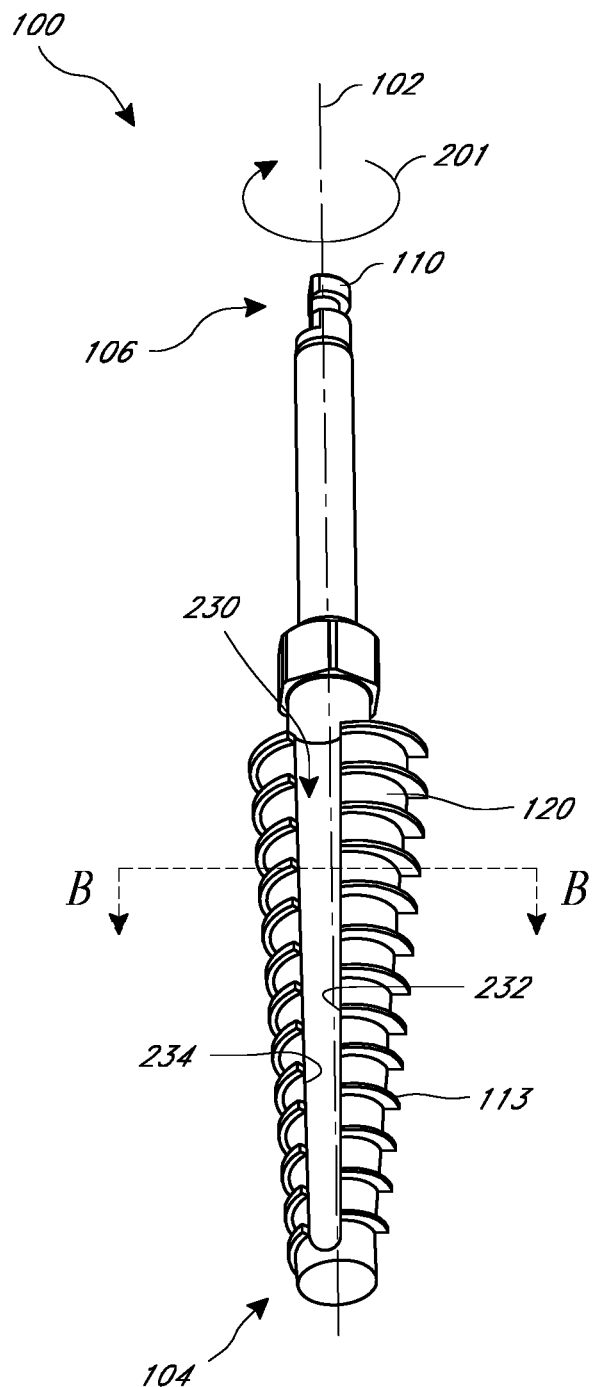
FIG. 3A is a side view of an embodiment of a drill bit.

FIG. 3A shows a non-limiting, illustrative embodiment of a drill bit 100 having certain features and advantages of the present disclosure. The drill bit 100 can have a longitudinal axis 102, an apical end 104, and a coronal end 106. In the illustrated embodiment, the drill bit 100 is tapered so that the outer dimension of the drill bit 100 decreases as the drill bit 100 extends toward the apical end 104, as shown in FIG. 3A. In some variants and embodiments, the drill bit 100 is not tapered. For example, in some embodiments, the outer dimension of the drill bit 100 can remain substantially constant as the drill bit 100 extends toward the apical end 104. The drill bit 100 can also include an attachment 110 by which the drill bit 100 can connected to a drilling machine (not shown) and/or handle (not shown). The attachment 110 can be at the coronal end 106 of the drill bit 100 and can be in certain embodiments coupled to the drill bit 100 and/or formed integrally with the drill bit 100. The drill bit 100 can be rotated about the longitudinal axis 102 as described below to form a hole in a patient's jawbone.

With continued reference to FIG. 3A, the drill bit 100 can have a guide thread 113 that extends radially outward from a drill bit core 120 of the drill bit 100. In the illustrated embodiment, drill bit core 120 is tapered so that the outer dimension of the drill bit core 120 decreases as the drill bit 100 extends toward the apical end 104. As with the drill bit 100, in other embodiments, the drill bit core can have substantially cylindrical or taper in a different manner. In the illustrated embodiment, the guide thread 113 is not a working tap but is instead configured to guide the drill bit 100 in and out of the bone in a controlled manner while allowing measurement of the insertion torque to determine the bone quality. In this way, the guide thread 113 can aid in providing an objective measurement of bone quality and thereby reduce error that may arise from a subjective determination of the clinician regarding bone quality. The guide thread 113 controls the insertion speed relative to the number of revolutions of the drill bit 100. The full insertion of the drill bit 100 in the bone is reached after a constant number of revolutions and therefore, after full insertion, the maximum torque measured by the drill unit or a torque wrench is directly related to the average bone quality over the length. The decision to use one drilling protocol over another can be based on the insertion torque of the drill bit 100. For example, if the insertion torque is below a certain level, the clinician may elect to use a drilling protocol that is designed for low-density bone. If the insertion torque is above a certain level, the clinician may elect to use a drilling protocol that is designed for high-density bone. In another embodiment, if the insertion torque of the drill bit 100 is below a certain level, the full insertion depth may not be needed (for example in case of soft bone), thus creating a shorter and smaller osteotomy. This would be the case in low quality or softer bone. For a human being, the bone density may vary from 16 g/cm3 (soft bone) to 80 g/cm3 (hard bone). In hard bone, the tool would be used to the full depth, thus creating a longer and larger osteotomy.

The guide thread 113 can be adapted to allow the drill bit 100 to be advanced into the bone in a controlled fashion, at a low speed (e.g., about 10-100 rpm), without irrigation, or a combination thereof. Low-speed drilling can generate less heat than high-speed drilling, making low-speed drilling potentially less harmful to the bone tissue than high-speed drilling. Drilling methods that avoid irrigation can have biological benefits for bone healing by not removing (e.g., washing) bone chips and blood out of the osteotomy.

Figure 3B:
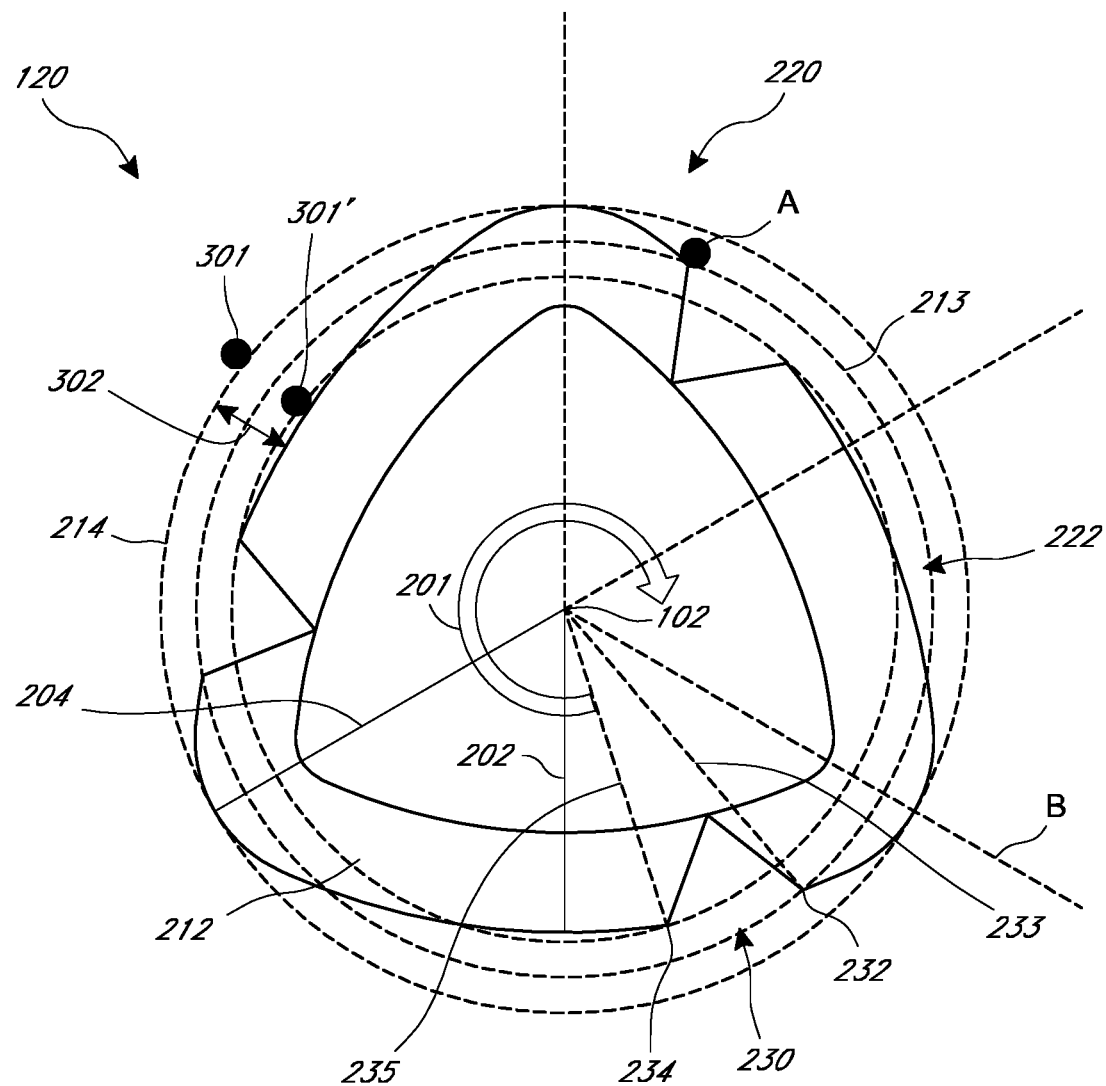
FIG. 3B is a transverse cross-sectional view of the drill bit of FIG. 3A.

FIG. 3B shows a transverse cross-sectional view of the drill bit core 120 of the drill bit 100 taken a point along the longitudinal axis 102 of the drill bit 100. For the sake of clarity, the guide thread 113 is not shown on the outer surface of the drill bit core 120 in the cross-sectional view. The drill bit core 120 can have a non-round or non-circular cross-sectional shape along a length l (in the longitudinal direction) of the drill bit 100 with the cross-sectional shape being taken along a plane that is generally perpendicular to the longitudinal axis 102 of the drill bit 100 as shown in FIG. 3A. In one embodiment, the drill bit core 120 has a non-round cross-sectional shape over the entire length of the drill bit core 120 (or of the portion of the drill bit 100 intended to be in contact with the bone) and in certain embodiments, the non-round cross-sectional shape can extend over 50 to 90% of the length of the drill bit core 120. In the illustrated embodiment, the shape of non-round cross-sectional shape of the drill bit core 120 can remain generally constant over the length of the drill bit core 120. For example, in an embodiment in which the drill bit core 120 tapers such that the outer dimension of the drill bit core 120 decreases as the drill bit 100 extends toward the apical end 104, the non-round cross-sectional shape of the drill bit core 120 can remain generally constant while changing in dimensions. In other embodiments, the drill bit core 120 can have more than one non-round cross-sectional shape over the length of the drill bit core 120.

The drill bit core 120 can have a minimum radius 202 and a maximum radius 204. The drill bit 100 can be rotated about the longitudinal axis 102, as indicated in FIG. 3B by the semi-circular arrow 201. As the drill bit 100 is rotated about the longitudinal axis 102, the minimum radius 202 will sweep out an inner circle 212, and the maximum radius 204 will sweep out an outer circle 214. Accordingly, a reference point on the surrounding bone will be pushed radially outward as the maximum radius 204 approaches the reference point. The reference point can reach a maximum displacement 301 when the maximum radius 204 arrives at the reference point. After the maximum radius 204 passes the reference point, the reference point can move radially inward to occupy the space vacated by the rotating drill bit 100. The reference point can reach a minimum displacement 301' when the minimum radius 202 arrives at the reference point. In this way, the surrounding bone can move back and forth across a working margin 302, as indicated by the double-headed arrow in FIG. 3B.

The drill bit 100 can form a compression zone 220 corresponding to the region of the drill bit 100 that compresses the surrounding bone. For example, in the illustrative embodiment shown in FIG. 3B (in which the drill bit 100 is rotating in the clockwise direction), the compression zone 220 extends from the maximum radius at the twelve o'clock position of the drill bit core 120 to the minimum radius at the two o'clock position of the drill bit core 120. The drill bit 100 can have a decompression zone 222 corresponding to the region of the drill bit 100 that allows decompression of the surrounding bone. For example, in the illustrative embodiment shown in FIG. 3B, the decompression zone 222 can extend from the minimum radius at the two o'clock position of the drill bit core 120 to the maximum radius at the four o'clock position of the drill bit core 120. In some variants, the drill bit 100 can include more than one compression zones 220 and decompression zones 222. For example, the tri-oval embodiment of FIG. 3B has three compression zones 220 and three decompression zones 222. Modified embodiments can include more or less compression zones and/or three compression zones with different shapes. Moreover, as noted above, the drill bit core 120 can have regions in which the non-round cross-sectional shape of the drill bit core 120 can be different or change. In addition, in the illustrated embodiment tri-oval embodiment includes three compression and decompression zones that have similar dimensions that fluctuate from the same maximum radius to minimum radius. However, in modified embodiments, the compression and decompression zones can fluctuate from maximum radii to minimum radii of different dimensions such that a different amount of compression and/or decompression occurs in each zone.

An aspect of certain embodiments of the disclosure is the recognition that the surrounding bone can have a recovery time defined as the time required for the surrounding bone to move from the maximum displacement 301 to the minimum displacement 301'. The recovery time of the surrounding bone can depend on the quality of the bone. For example, hard bone can have a shorter recovery time compared to soft bone. Thus, hard bone will tend to move more quickly from the maximum displacement 301 to the minimum displacement 301' than will soft bone. As discussed below, the drill bit 100 can be adapted to exploit the difference in recovery times between the hard and soft bone so that the drill bit 100 can selectively cuts hard bone while leaving soft bone intact or disproportionately cut hard bone as compared to softer bone.

The drill bit core 120 can include a cutting flute 230. The cutting flute 230 can have a cutting edge 232 and a trailing edge 234. The cutting edge 232 can be a cutting distance 233 from the longitudinal axis 102, which will be equal to the radius or rotation of the cutting edge 232. The trailing edge 234 can be a trailing distance 235 from the longitudinal axis 102, which will be the radius of rotation of the trailing edge 234. The cutting flute 230 can be positioned in the compression zone 220, as illustrated in FIG. 3B. Referring to FIG. 3B, by positioning the cutting flute 230 in the compression zone 220, the cutting distance 233 can be larger than the trailing distance 235.

The cutting edge 232 can be positioned within the working margin 302, as illustrated in FIG. 3B. In other words, the cutting distance 233 can be intermediate to the maximum displacement 301 and minimum displacement 301' of the surrounding bone. The cutting edge 232 can sweep out a cutting circle 213 that can be interposed between the inner and outer circles 212, 214 that are swept out by the minimum and maximum radii of the drill bit core 120. The region between the outer circle 214 and the intermediate circle 213 represents a "no-cutting" zone because bone in this region will not encounter the cutting edge 232 as the cutting edge 232 passes by the bone. In some embodiments, the width of the "no-cutting" zone can be about 50 µm. The region between the intermediate circle 213 and the inner circle 212 represents a "cutting" zone because bone in this region will be cut by the cutting edge 232 as the cutting edge 232 passes by the bone.

The circumferential placement of the cutting edge 232 and the rotational speed of the drill bit 100 can be adjusted so that as the cutting edge 232 passes by the bone, the hard bone has had sufficient time to enter the "cutting" zone while the slower recovering soft bone remains in the "no-cutting" zone. A rotation time (RT) can be defined as the time needed for the cutting edge 232 to travel the distance between the cutting edge 232 and the preceding maximum of the drill bit core 120. Referring to FIG. 3B, RT would be equal to the time needed for point A to travel to line B. A soft bone recovery time (SBRT) can be defined as the time needed for the soft bone to return from the outer circle 214 to the intermediate circle 213. A hard bone recovery time (HBRT) can be defined as the time needed for hard bone to return from the outer circle 214 to the intermediate circle 213. The drill bit 100 and drill speed (e.g., rpm) can be tuned so that two criteria are met: (1) SBRT>RT, thereby avoiding cutting soft bone; and (2) HBRT<RT, thereby cutting hard bone. Parameters that can be considered when designing the drill bit 100 include: the difference in recovery times between hard and soft bone, the difference between the maximum radius of the drill bit core 120 and the radius of the cutting edge 232, the circumferential placement of the cutting flute 230, the rotational speed of the drill bit 100, the rate of radial change of the outer surface of the drill bit core 120, and the insertion speed of the drill bit 100.

Figure 4A:
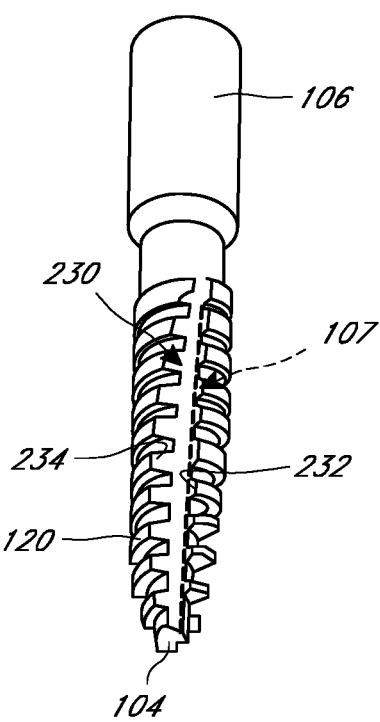
FIGS. 4A-4D are perspective views of illustrative embodiments of a drill bit.
Figure 4B:
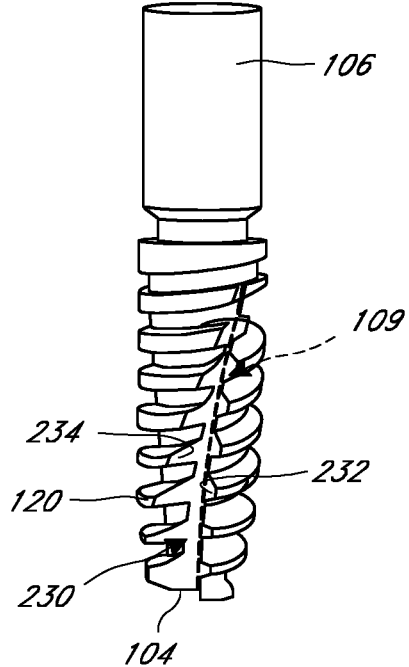

Referring to FIGS. 4A-4B, the drill bit 100 of the present disclosure can include different configurations of the drill bit core 120. For example, the drill bit 100 can include a plurality of tri-oval drill bit cores 120 that are interlinked in a helical configuration to form a screw-like structure that extends to the apical end 104 of the drill bit 100. The drill bit cores 120 of the illustrated drill bit 100 can taper in the apical direction. However, in some variants, the outer dimension of the drill bit cores 120 can remain substantially constant along the length of the drill bit 100.

As shown in FIG. 4A, in an embodiment, the cutting edges 232 of the drill bit core 120 can be aligned with one another along a line 107 that extends from the apical end 104 toward the coronal end 106 of the drill bit 100, thereby forming a straight or substantially straight cutting flute 230 in which the line 107 extends generally parallel to the longitudinal axis 102 of the drill bit 100. As shown in FIG. 4B, in some variants, the cutting edges 232 of the drill bit core 120 can be aligned with one another along a curve 109 that extends from the apical end 104 toward the coronal end 106 of the drill bit 100, thereby forming a curved cutting flute 232. The drill bit core 120 can taper or can have a substantially constant outer dimension along the length of the drill bit 100. In the illustrated embodiment, the curve 109 bends generally in the same direction of a helical thread on the drill bit core 120 (e.g., counter-clockwise toward the coronal end 106). In some variants, the curve 109 can bend generally in the direction opposite of the helical thread of the drill bit cores 120.

Figure 4C:
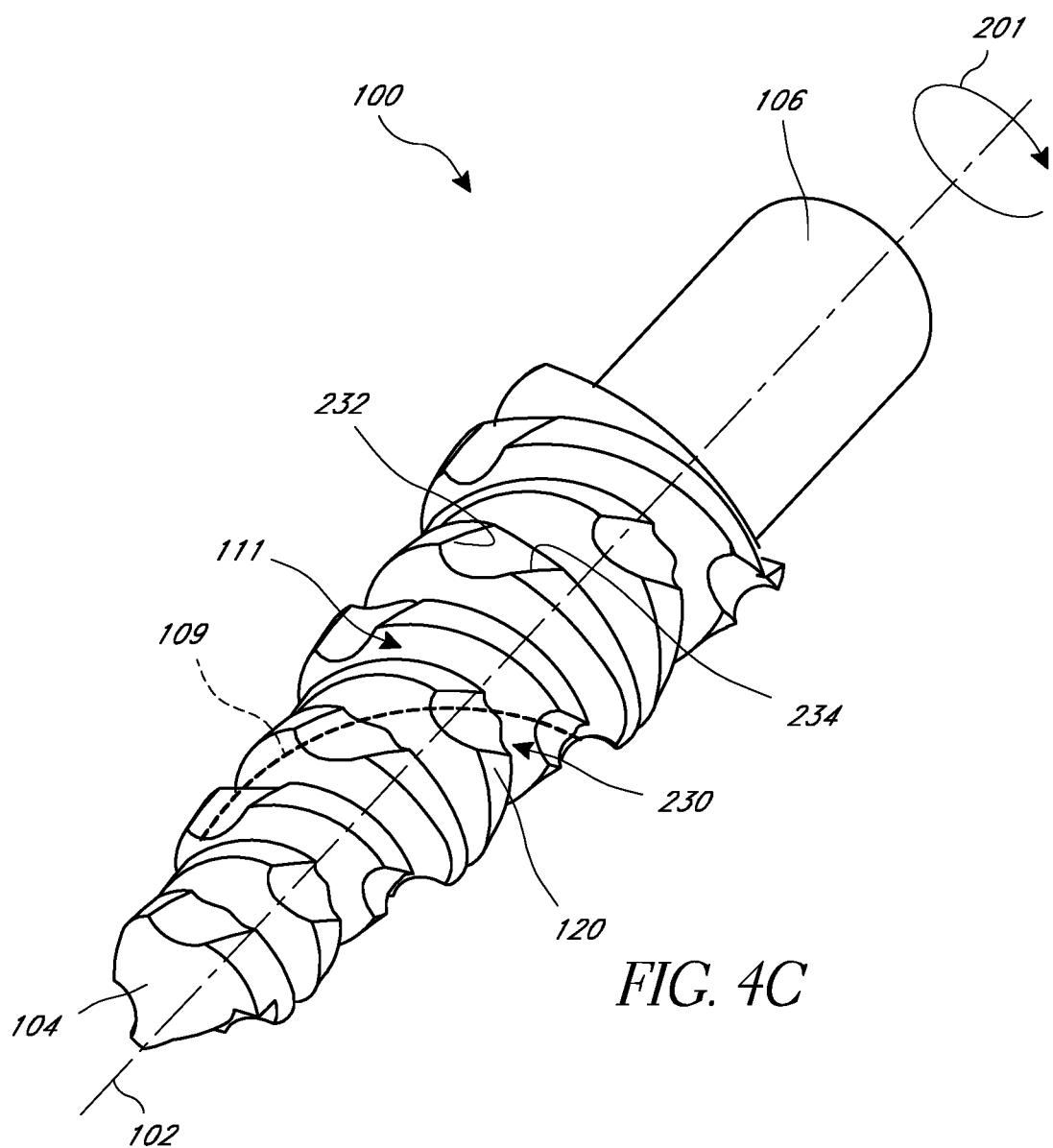

Referring to FIG. 4C, the drill bit 100 can include a plurality of planar tri-oval drill bit cores 120 that are aligned substantially perpendicular to the longitudinal axis 102 of the drill bit. The planar tri-oval drill bit cores 120 can be spaced apart from one another, thereby forming a gap 111 between adjacent planar tri-oval drill bit cores 120. In the illustrated embodiment, the drill bit cores 120 near the apical end 104 of the drill bit 100 have a smaller outer dimension than the drill bit cores 120 toward the coronal end 106 of the drill bit. In other words, the drill bit 100 tapers toward the apical end 104. However, in some variants, the outer dimension of the drill bit cores 120 can remain substantially constant along the length of the drill bit 100. In the illustrated embodiment, the cutting surfaces 232 of adjacent drill bit cores 120 are circumferentially shifted relative to one another so that the cutting surfaces 232 lie along a curve 109, thereby forming a disjointed cutting flute 230 that spirals around the outer surface of the drill bit 100. In some variants, the cutting surfaces 232 of the plurality of planar tri-oval drill bit cores 120 align with one another along a line, as described above with regard to FIG. 4A.

Figure 4D:
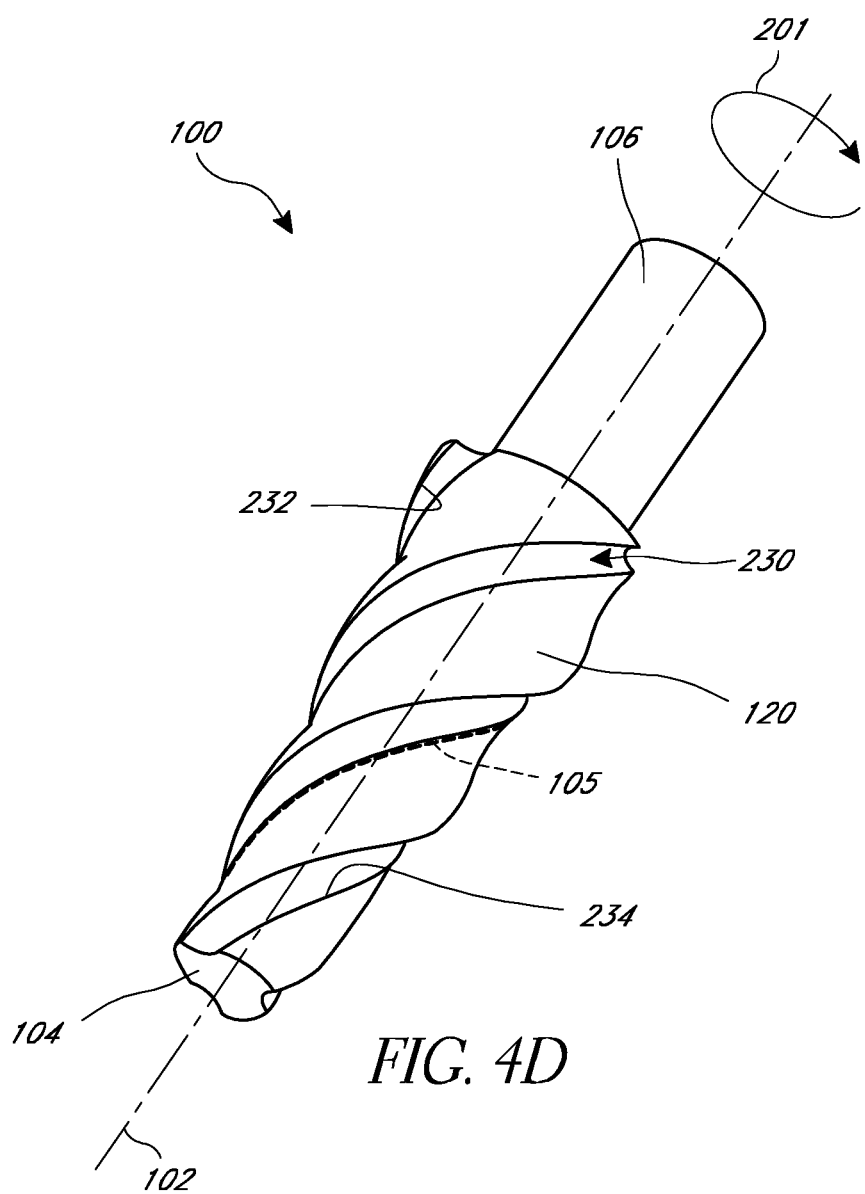

Referring to FIG. 4D, the maximum outer dimension of the drill bit core 120 can taper and shift circumferentially in the apical direction in an uninterrupted manner, thereby producing a spiraling and continuous cutting flute 230. A spiraling cutting flute can facilitate removal of cut material (e.g., bone chips) from the osteotomy, as discussed below. In the illustrated embodiment, the position of the cutting edge 232 relative to the maximum outer dimension of the drill bit core 120 remains substantially fixed along the length of the drill bit 100. As shown in FIG. 4D, the trailing edge 234 can align along a curve 105 that spirals around the longitudinal axis 102. The cutting edge 232 can also align along a curve that is substantially parallel to the curve 105.

The drill bit 100 of the present disclosure can include various configurations of the cutting edge 232 and of the maximum and minimum dimensions of the drill bit core 120. For example, the position of the maximum and minimum outer dimensions of the drill bit cores 120 can be aligned along the length of the drill bit, as shown in FIG. 4A. In certain variants, the position of the maximum and minimum outer dimensions of the drill bit cores 120 can shift circumferentially along the length of the drill bit, as shown in FIG. 4C. The position of the cutting edge 232 relative to the maximum outer dimension of the drill bit cores 120 can remain constant along the length of the drill bit 100, as shown in FIG. 4A. The position of the cutting edge 232 can shift toward or away from the maximum outer dimension of the drill bit core 120. In some variants, both the position of the maximum outer dimension of the drill bit cores 120 and the position of the cutting edge 232 relative to the maximum outer dimension of the drill bit core 120 can shift circumferentially along the length of the drill bit 100. Moreover, the aforementioned variations of the drill bit core 120 can be achieved on a drill bit core 120 that is continuous along the length of the drill bit 100 (as in FIG. 4D) or on a drill bit core 120 that is discontinuous (as in FIG. 4C).

Figure 5A:
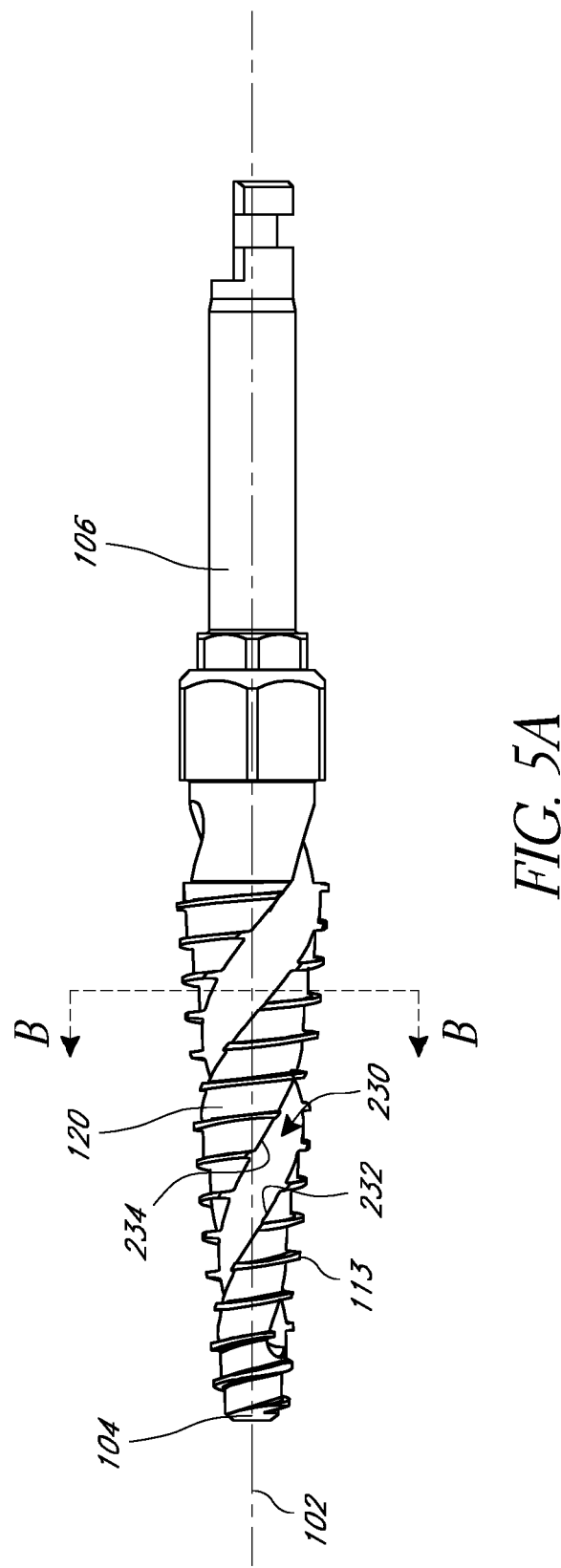
FIG. 5A is a side view of an embodiment of a drill bit.
Figure 5B:
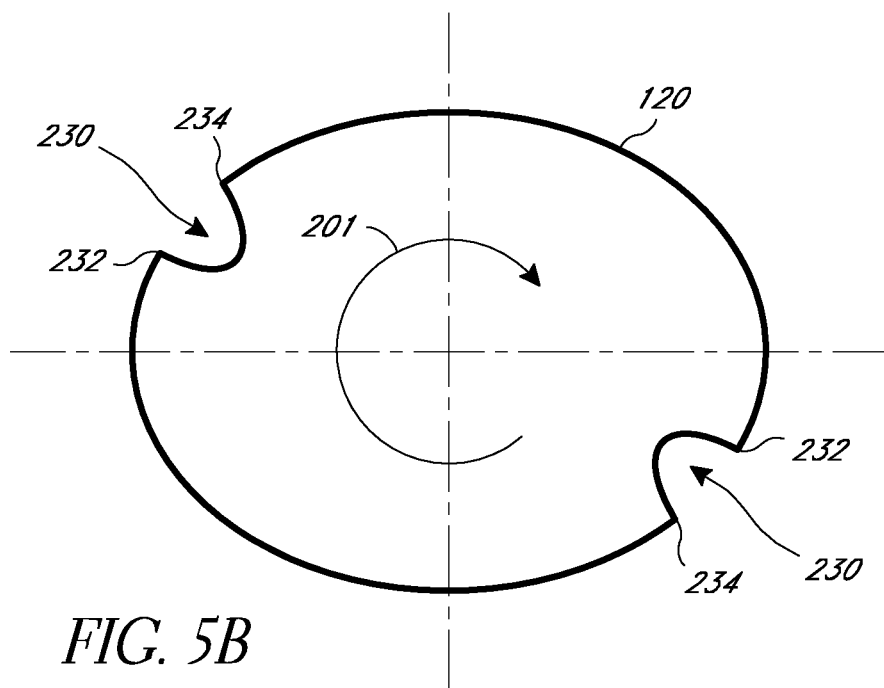
FIG. 5B is a transverse cross-sectional view of the embodiment of FIG. 5A.

FIG. 5A is a non-limiting, illustrative embodiment of the drill bit 100 having an oval-shaped drill bit core 120. FIG. 5B shows a cross-section of the drill bit core 120 along a plane that is perpendicular to the longitudinal axis 102 of the drill bit 100. The maxima of the oval-shaped drill bit core 120 can be twisted in sync with the cutting flute 230. The guide thread 113 can have a height that is defined as the distance the guide thread 113 extends radially away from the drill bit core 120. The guide thread 113 can have a substantially round profile, e.g., a substantially circular profile, while the core 120 can have an oval-shaped profile. Thus, the height of the guide thread 113 can vary along the circumference of the drill bit core 120, with the height of the guide thread 113 being greatest at the minima of the oval-shaped drill bit core 120 and the height of the guide thread 113 being least at the maxima of the oval-shaped drill bit core 120.

Figure 5C:
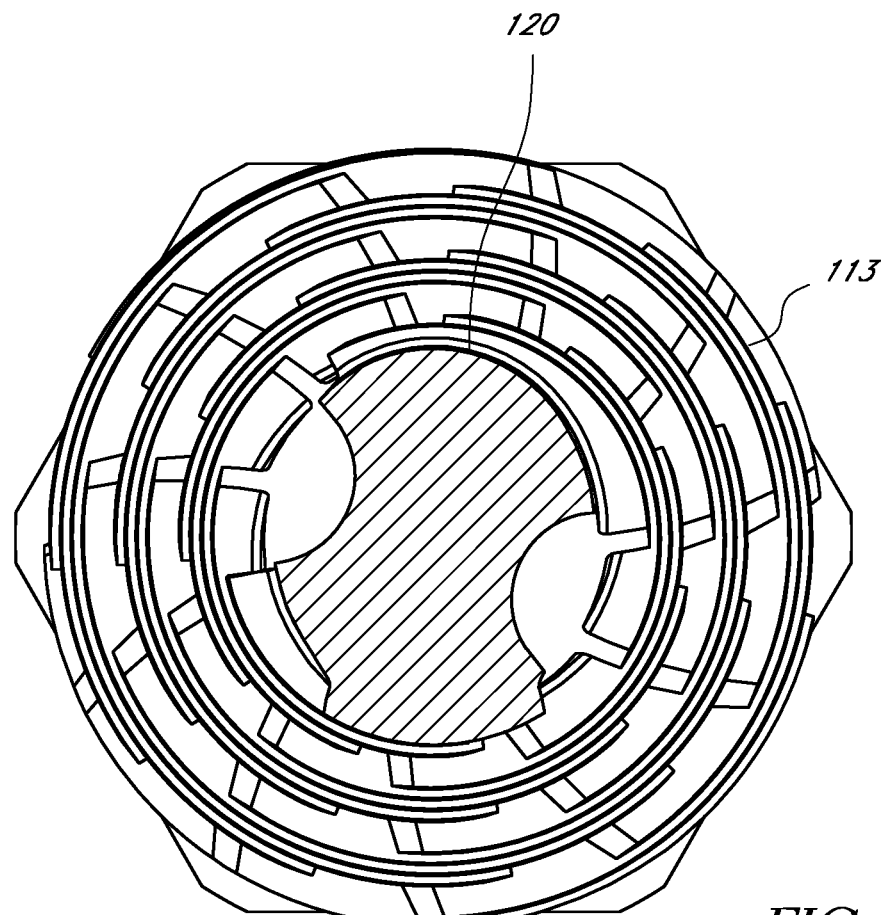
FIG. 5C is an apical end view of the embodiment of FIG. 5A.

FIG. 5C is an end view of the drill bit 100 from the apical end 104. As shown in FIG. 5C, as the drill bit 100 tapers in the apical direction, the ovality of the drill bit core 120 can increase in the apical direction. The apical tip of the drill bit 100 can have the highest eccentricity. The eccentricity (ratio between the maximum and minimum radii of the drill bit core 120) is a consequence of the ovality, which is the absolute difference between the maximum and minimum radii of the drill bit core 120. In other words, the transverse cross-section of the drill bit core 120 can be more round toward the coronal end 106 of the drill bit 100 compared to the transverse cross-section of the drill bit core 120 toward the apical end 104 of the drill bit 100. This is because in some variants the working margin 302 (shown in FIG. 3B) can be substantially constant along the length of a drill bit 100 that tapers toward the apical end 104. For example, in the illustrated embodiment, the working margin 302 can remain about 150 µm along the length of the drill bit 100, while the outer diameter of the drill bit core 120 can taper from about 4 mm at the coronal end 106 of the drill bit to about 2 mm at the apical end 104 of the drill bit. At the apical tip, the cutting edge 232 can be at about 40° from the maximum radius of the oval-shaped drill bit core 120. In one embodiment, the eccentricity can vary over the full length of the drill bit core 120 such that it is higher at the apical tip. In another embodiment, the apical tip has a round shape at least on a portion of the length of the drill core 120 to allow insertion of the drill bit and because very little cutting occurs at the tip. The eccentricity can increase after the round apical section and then decrease toward the coronal end. This round section can extend, for example up to 2 mm along the longitudinal axis of the implant from the apical end 104 of the drill bit.

Figure 6:
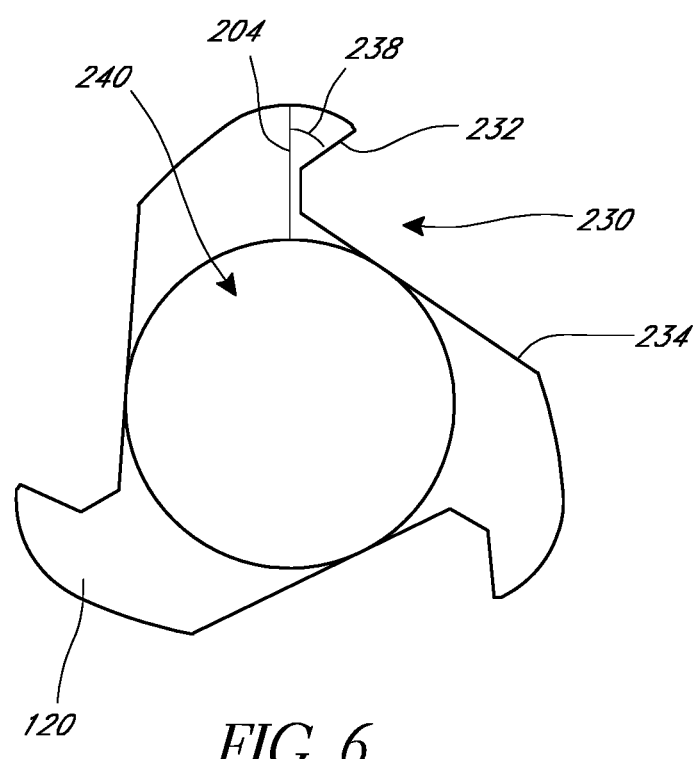
FIG. 6 is a transverse cross-sectional view of an embodiment of a drill bit.

Referring to FIG. 6, the attack angle of the cutting edge 232 can be modified to make the drill bit 100 more or less aggressive at cutting the surrounding bone. In the illustrated embodiment, the cutting edge 232 forms and angle 238 of about 50° with the maximum radius 204 of the drill bit core 120. In some embodiments, the angle 238 can be at least about: 10°, 20°, 30°, 40°, 50°, or otherwise. In certain variants, the cutting flute 230 can be made larger by moving the cutting edge 232 and trailing edge 234 apart from one another. In some embodiments, the cutting flute 230 can be made large in order to accommodate bone chips that are cut by the cutting edge 232. In some variants, the drill bit 100 can include a cavity 240 for collecting bone chips that are cut from the surrounding bone by the cutting edge 232. In other embodiments, the cutting edge can be placed on the maximum radii.

In the illustrated embodiment of FIG. 6, the cutting edge 232 has been positioned near to the maxima of the drill bit core 120. As discussed above, by positioning the cutting edge 232 closer to the maxima of the drill bit core 120, RT can be increased because it can take longer for the cutting edge 232 to arrive at the site of the bone that was compressed by the preceding maxima. Also, by positioning the cutting edge 232 closer to the maxima, the cutting distance 233 (shown in FIG. 3B) can be enlarged. Enlarging the cutting distance 233 can reduce SBRT and HBRT because the distance from the maximum displacement 301 to the cutting zone is reduced. Thus, the combined effect of a longer RT and a shorter SBRT can result in more soft bone being cut by the drill bit 100. Similarly, the combined effect of a longer RT and a shorter HBRT can result in more hard bone being cut by the drill bit 100. The illustrated drill bit 100 is an aggressive tri-oval drill bit 100 that may cut soft bone as well as hard bone, although the extent of hard bone cutting can be greater than the extent of soft bone cutting because hard bone will recover faster and therefore extend further into the cutting zone than will the soft bone.

Figures 7A, 7B:
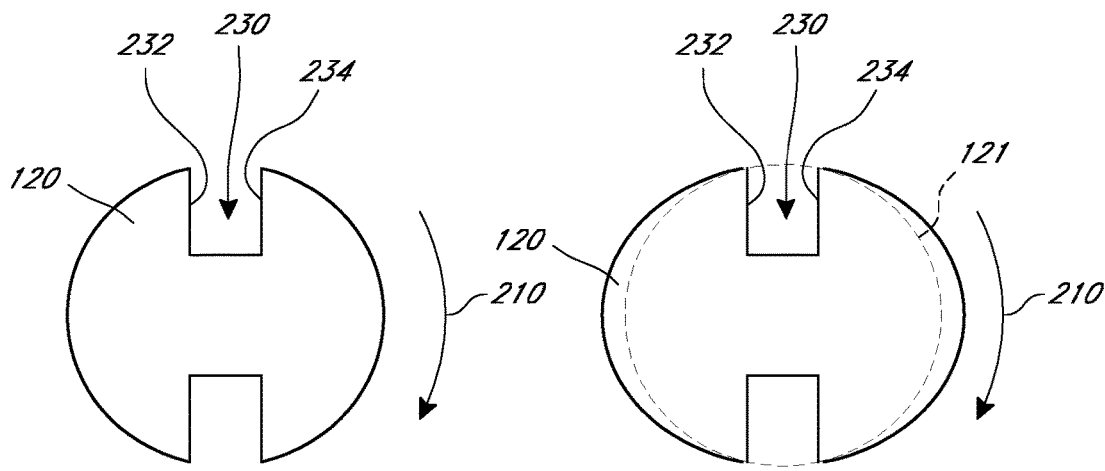
FIGS. 7A-7D are transverse cross-sectional views of illustrative embodiments of a drill bit.
Figure 7C:
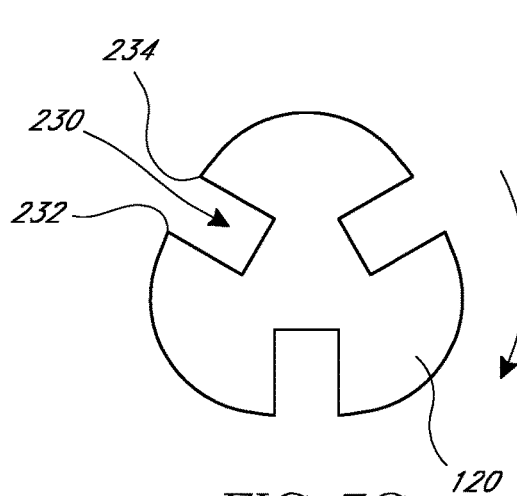
Figure 7D:
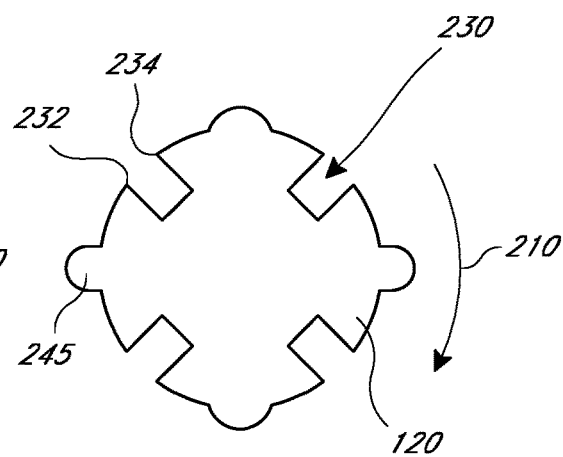

Referring to FIGS. 7A-7D, the drill bit core 120 of the drill bit 100 can have different cross-sectional shapes. The cross-sectional shape of the drill bit core 120 can be configured to minimize cutting soft bone, minimize friction, minimize heat, and/or maximize directional control (e.g., avoid wobbling) or maximize cutting of hard bone. In the illustrated embodiments, the direction of rotation of the drill bit core 120 is indicated by the arrow 210. FIG. 7A shows a drill bit core 120 having a substantially rounded profile. The radial distance of the cutting edge 232 is substantially equal to the radial distance of the trailing edge 234. In the shown embodiment, the drill bit core 120 has two cutting flutes 230 that are circumferentially spaced 180° apart from one another. FIG. 7B shows an oval-shaped drill bit core 120 having two cutting flutes 230 that are circumferentially spaced 180° apart from one another, with the radial distance of the cutting edge 232 being substantially equal to the radial distance of the trailing edge 234. In some variants, the ovality of the drill bit 120 can be small as indicated by the dashed core 121. FIG. 7C shows a tri-oval drill bit core 120 having three cutting flutes 230 circumferentially spaced about 120° apart from an adjacent cutting flute 232. In the illustrated embodiment, the radial distance of the cutting edge 232 is substantially equal to the radial distance of the trailing edge 234. FIG. 7D depicts a cruciform drill bit core 120 having four cutting flutes 230 circumferentially spaced about 90° apart from an adjacent cutting flute 232. In the illustrated embodiment, the radial distance of the cutting edge 232 is substantially equal to the radial distance of the trailing edge 234. As shown in FIG. 7D, the drill bit core 120 can include one or more protrusions 245. In some variants, the protrusion 245 can extend radially beyond the radial distance of the cutting edge 232 by about 50 µm.

Figure 8A:
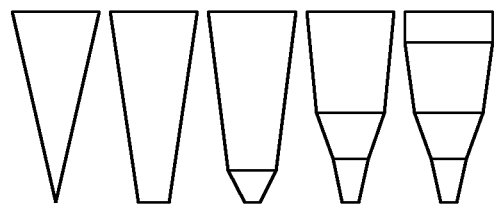
FIGS. 8A-8C are side views of illustrative embodiments of a drill bit.
Figure 8B:
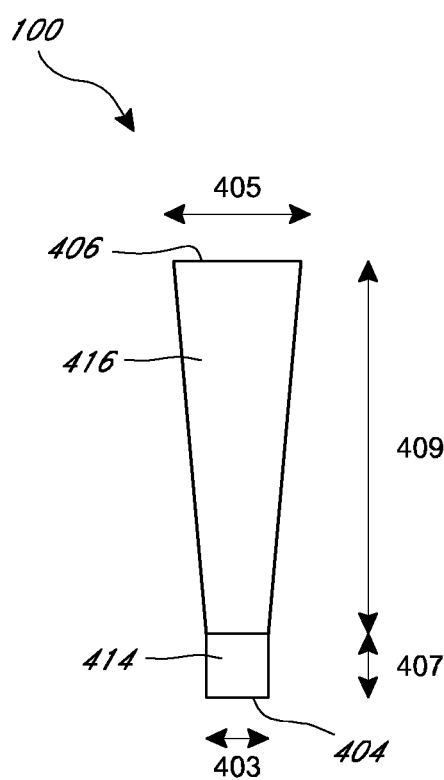
Figure 8C:
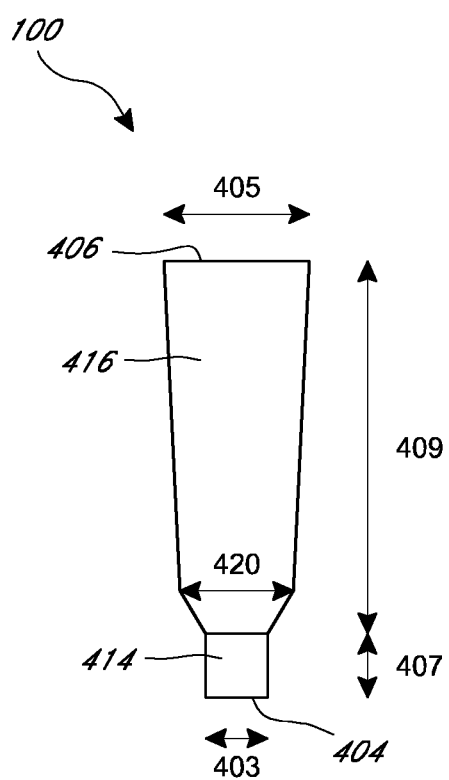

Referring to FIGS. 8A-8C, the drill bit 100 can have a variety of macro-shapes. The macro-shape of the drill bit 100 can be defined by the outer dimension of the drill bit core 120 along the longitudinal axis 102 of the drill bit 100. The shape of the osteotomy will match the macro-shape of the drill bit 100 that was used to produce the osteotomy. Referring to FIG. 8A, the macro-shape of the drill bit 100 can be tapered in the apical direction. The taper can be pointed or blunted. The taper can be constant along the length of the drill bit 100. The taper can vary along the length of the drill bit 100. For example, the taper in some regions of the drill bit 100 may be steeper than in other regions of the drill bit 100.

In some embodiments, the macro-shape of the drill bit 100 is selected to match the macro-shape of the implant. As shown in FIG. 8B, the drill bit 100 can have an apical base 404 and a coronal base 406. The apical base 404 is the apical-most surface of an apical portion 414, and the coronal base 406 is the coronal-most surface of a coronal portion 416, as shown in FIG. 8B. In some variants, the coronal base 406 can have an outer dimension 405 that is greater than the outer dimension 403 of the apical base 404. For example, in the illustrated embodiment, the drill bit 100 can have a coronal base 406 that has an outer dimension 405 of about 3.2 mm wide and an apical base 404 that has an outer dimension 403 of about 2 mm wide. The coronal portion 416 can taper in the apical direction while the apical portion has a substantially constant width. The coronal portion 416 can have a longitudinal length 409 and the apical portion 414 can have a longitudinal length 407. In some embodiments, the coronal portion 416 has a longitudinal length 409 of about 13 mm and the apical portion 414 has a longitudinal length 407 of about 2 mm.

Referring to FIG. 8C, the drill bit 100 can have an intermediate portion 418 interposed between the coronal portion 416 and the apical portion 414. In some embodiments, the drill bit 100 can have more than one intermediate portion 418, as shown in the embodiment on the far right of FIG. 8A. The intermediate portion 418 can have a coronal surface 420 that is the coronal-most portion of the intermediate portion 418. In the embodiment depicted in FIG. 8C, the drill bit 100 can have a coronal base 406 that has a width of about 3.8 mm, a coronal surface 420 that is about 3.2 mm, and an apical base 404 that is about 2 mm. The longitudinal length of the coronal portion 416 can be about 12 mm, the longitudinal length of the intermediate portion 418 can be about 1 mm, and the longitudinal length of the apical portion 414 can be about 2 mm.

Figure 9:
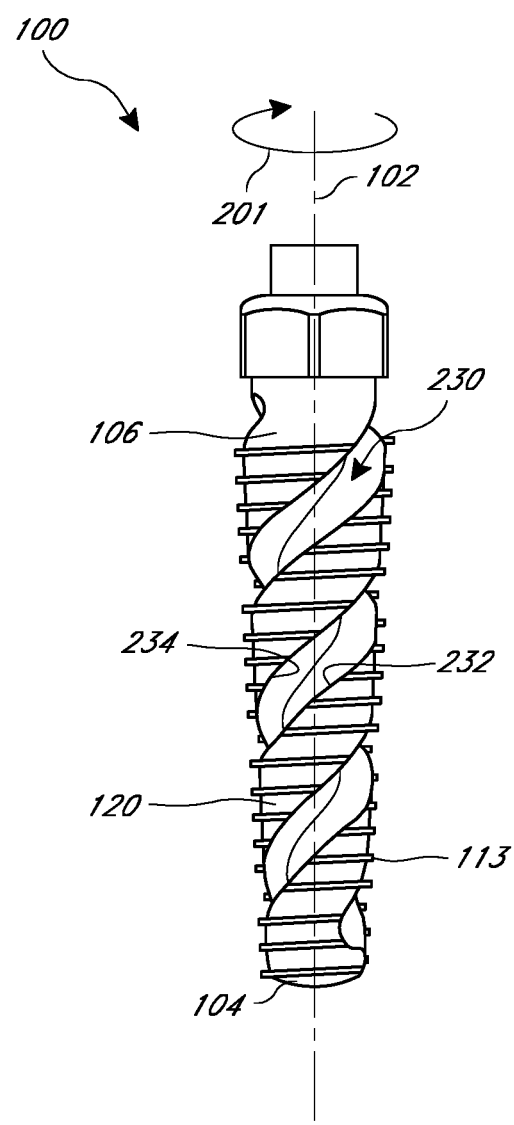
FIG. 9 is a side view of an embodiment of a drill bit.

FIG. 9 depicts a non-limiting, illustrative embodiment of the drill bit 100 having a twisted and tapered oval drill bit core 120, as described above. In some variants, the cutting flute 230 can be adapted to transport cut bone out of the osteotomy. For example, in the illustrated embodiment, the cutting flute 230 has a spiral configuration at a pitch of about 45°. The pitch of the cutting flute 230 can be selected so that bone chips do not get stuck in the cutting flute 230 and are transported out of the osteotomy. In the illustrated embodiment, the cutting flute 230 wraps in the direction of rotation of the drill bit 100, which is clockwise toward the apical end 104. This configuration can transport bone chips toward the coronal end 106 of the drill bit 100 and out of the osteotomy when the drill bit 100 is rotated in the direction for cutting bone. The depicted embodiment has guide threads 113 with a round profile. The guide threads 113 can be substantially perpendicular to the longitudinal axis 102, as shown in FIG. 9. In some variants, the guide threads 113 can be angled toward the apical end 104 of the drill bit 100. As the function of the guide threads 113 is only to control the insertion of the tool and not cut a thread for the implant to be subsequently placed, the pitch of the guide thread does not match the one of the implant. This has the advantage that the user does not have to be concerned about following the same thread path.

Figure 10:
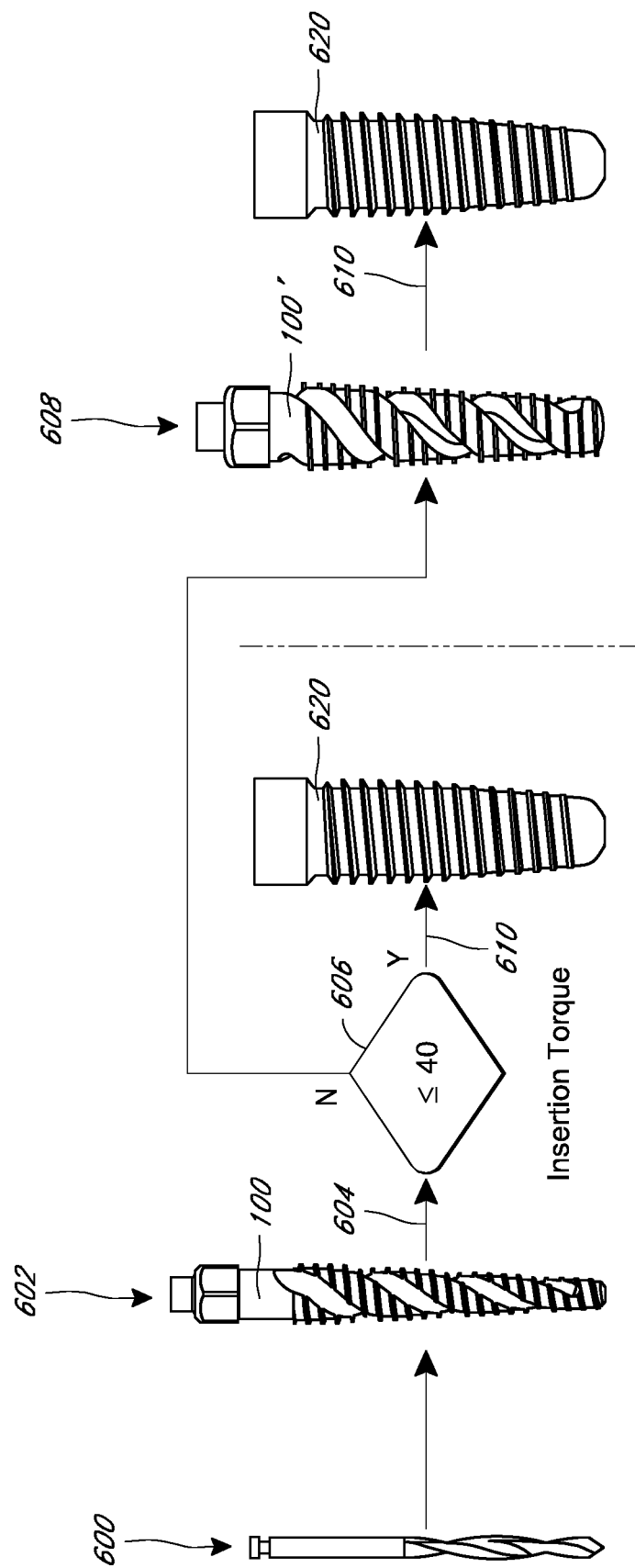
FIG. 10 is a schematic representation of a method of implanting an implant into a bone.

FIG. 10 depicts a schematic of an embodiment of a method of use of the drill bit 100 of an embodiment of the present disclosure to prepare an osteotomy for receiving an implant. As discussed, the drill bit 100 can be adapted to reduce the number of tools and/or steps needed to prepare the osteotomy. The procedure of preparing an osteotomy for receiving an implant may be referred to herein as "normalizing" the bone. The drill bit 100 can be adapted to normalize the bone with the use of only one drill bit 100. In some variants, two or more drill bits 100 can be used to normalize the bone. As shown in FIG. 10, the method may include a step 600 in which a hole is drilled into the bone using a pilot drill bit that has a diameter smaller than the drill bit 100. In some embodiments, the pilot step 600 uses a pilot drill bit having a diameter of 2 mm. The pilot step 600 can be performed using irrigation. The drill speed in step 600 can be about 800 rpm.

Still referring to FIG. 10, the method of preparing the osteotomy for receiving an implant can include a normalizing step 602. A first drill bit 100 according to an embodiment described herein can be used in the normalizing step 602. The first drill bit 100 can be selected based on the implant that will be implanted into the osteotomy. In some variants, the first drill bit 100 can be used to enlarge the hole created by a drilling step 600. In certain variants, the normalizing step 602 can be performed without performing a preceding drilling step 600. The normalizing step 602 can be performed with or without irrigation. The normalizing step 602 can be performed using a drill speed of about 50 to 100 rpm. In some variants, the normalizing step 602 can include a measuring step 604 that determines the insertion torque. The measuring step 604 can determine the insertion torque by sensing the torque applied to the drill bit 100. The measuring step 604 can include an evaluating step 606 that evaluates whether the normalization of the bone is successful. In some variants, the evaluating step 606 can compare an actual insertion torque as measured in the measuring step 604 with a desired insertion torque. The desired insertion torque can be determined by a look-up table that correlates implant success to insertion torque. In some variants, the normalization can be adequate when the insertion torque is less than or equal to about 40 Ncm. In some embodiments, the desired insertion torque may be modified based on the type of implant that is intended to be installed in the osteotomy.

The method of preparing the osteotomy for receiving an implant can include a further normalizing step 608. The further normalizing step 608 can be performed using a second drill bit 100' according to an embodiment described herein. The second drill bit 100' can have a different macro-shape compared to the first drill bit 100. The second drill bit 100' can have a different configuration of the drill bit core 120 compared to the first drill bit 100. The method of preparing the osteotomy for receiving an implant can be iterative. For example, the method can proceed from the further normalization step 608 to the measuring step 604 and the evaluating step 606 multiple times until the normalization is adequate to receive an implant.

In another embodiment during the normalization step 602 the torque is measured, by a drilling unit or controller connected to the drill bit 100, at or until a predefined length of the drill bit 100 has been inserted into the hole created by a drilling step 600. Said predefined length can be controlled mechanically, for example, the drill bit can have a removable stop whose position is calibrated for soft bone indicating the maximum drilling length for the torque measurement. Alternatively, the predefined length can be controlled by a software of the drill unit measuring the torque. If the torque measured until or at said predefined length is above a certain value indicating the presence of hard bone, then the drill unit can indicate to the user to continue drilling beyond the predefined length. The removable stop can be removed and drilling resumes until a second fixed stop, whose position is calibrated for hard bone. If the torque measured until or at said predefined length is below a certain value indicating the presence of soft bone the drill unit can indicate to the user to stop drilling and to start implanting an implant 620. Furthermore the drill unit can be provided with a screen or any kind of user interface indicating to the user the quality of the bone to help the decision. The type of bone can also be indicated by the drilling unit to the user using and audible signal such as an alarm. Alternatively the drilling unit can directly control the insertion depth based on the torque measured and stop the drilling with first drill bit 100 after a specified number of turns.

The drill bit 100 of the present disclosure can be used in a method of implanting an implant into a jaw bone 30 (shown in FIG. 1). The method of implanting an implant into a jaw bone 30 can include the method of preparing the osteotomy for receiving an implant described above. The method of implanting an implant into a jaw bone 30 can include an installing step 610. The installing step 610 can include implanting an implant 620 into an osteotomy prepared with the drill bit 100. The installing step can be performed with or without irrigation. The installing step 610 can be performed at a rotational speed of the implant 620 of about 50 rpm. In some variants, the installing step 610 can be performed at a rotational speed of the implant 620 of about 25 rpm.

Figure 11:
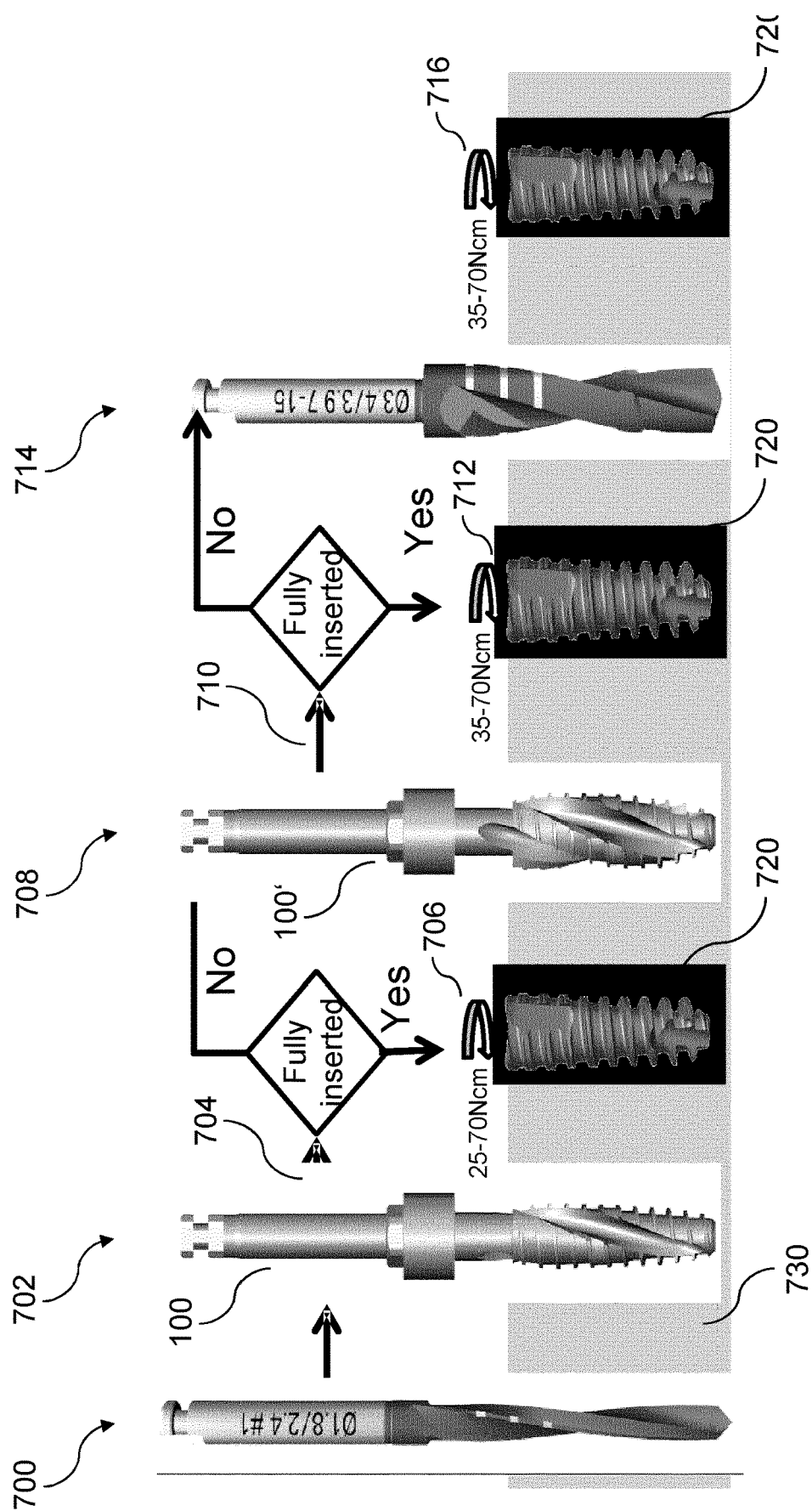
FIG. 11 is a schematic representation of another method of implanting an implant into a bone.

FIG. 11 is a schematic representation of another embodiment of a method of use of the drill bit 100 of an embodiment of the present disclosure to prepare an osteotomy for receiving an implant. As is shown in FIG. 11, the method may include a pilot step 700 in which a hole is drilled into the jaw bone 730 using a pilot drill bit that has a diameter smaller than the drill bit 100. The hole created in the pilot step 700 serves as a guiding hole for the following steps. The hole created in the pilot step 700 may be an underprepared site. The pilot step 700 can be performed using irrigation. The drill speed in the pilot step 700 can be about 800 rpm. For example, the pilot drill bit used in the pilot step 700 may have a diameter in the range of 1.8 to 2.4 mm. In some embodiments, the pilot step 700 uses a pilot drill bit having a diameter of 2 mm.

Still referring to FIG. 11, the method of preparing the osteotomy for receiving an implant can include a first normalizing step 702. A first drill bit 100 according to an embodiment described herein can be used in the first normalizing step 702. The first drill bit 100 can be selected based on the implant that will be implanted into the osteotomy. In some variants, the first drill bit 100 can be used to enlarge the hole created by the pilot step 700. In certain variants, the first normalizing step 702 can be carried out without performing a preceding drilling step 700. The first normalizing step 702 can be performed with or without irrigation. The first normalizing step 702 can be performed using a drill speed of about 50 to 100 rpm, in particular, using a drill speed of about 50 rpm.

In particular, the first drill bit 100 may be configured such that the first cutting edge is a first radial distance from the longitudinal axis and a maximum outer dimension of the drill bit core is a second radial distance from the longitudinal axis, wherein the second radial distance is larger than the first radial distance. The drill bit core of the first drill bit 100 may have a no-cutting zone defined as the difference between the second radial distance and the first radial distance.

The method illustrated in FIG. 11 may comprise a first evaluating step 704 in which it is evaluated whether the first drill bit 100 can be fully inserted into the osteotomy in the first normalizing step 702. In this first evaluating step 704, it is determined whether the first drill bit 100 is properly inserted into the osteotomy, i.e., inserted along a sufficient length of the first drill bit 100, and the torque applied to the first drill bit 100 is measured. Based on the results of this evaluation, i.e., on the results of determining the insertion length or depth and of measuring the applied torque, the next steps are selected, as will be further detailed in the following.

For example, in order to determine whether the first drill bit 100 is properly inserted, the first drill bit 100 may be provided with a marking, such as a shoulder, which indicates an insertion length of the first drill bit 100 that is equal or at least similar to the length of the implant 720 to be implanted into the osteotomy. If it is found that, in the first normalizing step 702, the first drill bit 100 has been inserted into the osteotomy along such a length that the marking is arranged at the coronal end of the osteotomy, it is determined that the first drill bit 100 is inserted along a sufficient length.

The torque applied to the first drill bit 100 can be measured, for example, by a drilling unit or a controller connected to the first drill bit 100, e.g., when or until a predefined length of the first drill bit 100 has been inserted into the hole created in the pilot step 700. In some variants, the first evaluating step 704 can compare an actual insertion torque as measured in this step with a desired insertion torque. The desired insertion torque can be determined by a look-up table that correlates implant success to insertion torque. In some variants, the normalization can be adequate when the insertion torque is less than or equal to about 40 Ncm. In some embodiments, the desired insertion torque may be modified based on the type of implant that is intended to be installed in the osteotomy.

If the first evaluating step 704 provides a positive result, i.e., a result indicating that the first drill bit 100 has been inserted along a sufficient length and the measured torque has a desired value, an installing step 706 is performed. In the installing step 706, the implant 720 is inserted into the osteotomy prepared with the drill bit 100. The installing step 706 can be performed with or without irrigation. The installing step 706 can be performed at a rotational speed of the implant 720 of about 50 rpm. In some variants, the installing step 706 can be performed at a rotational speed of the implant 720 of about 25 rpm. In the installing step 706, the implant 720 may be inserted into the jaw bone 730 under the application of an insertion torque in the range of about 25 to 70 Ncm (see FIG. 11).

If the first evaluating step 704 provides a negative result, a second normalizing step 708 is performed. The second normalizing step 708 can be performed using a second drill bit 100' according to an embodiment described herein. The second drill bit 100' can have a different macro-shape compared to the first drill bit 100. The second drill bit 100' can have a different configuration of the drill bit core 120 compared to the first drill bit 100.

In particular, the second drill bit 100' may be configured such that the first cutting edge is arranged at a maximum of the non-round or non-circular portion of the drill bit core or arranged so as to be circumferentially spaced from a maximum of the non-round or non-circular portion of the drill bit core in a direction which is opposite to the rotation direction in which the second drill bit 100' is rotated when inserting it into the osteotomy.

The second drill bit 100' may be configured such that the first cutting edge is disposed outside the first compression zone of the drill bit core.

The method of preparing the osteotomy for receiving an implant can be iterative. For example, the method can proceed from a further normalization step, e.g., the second normalizing step 708, to an evaluating step, which may be performed in substantially the same or a similar manner as the first evaluating step 704, multiple times until the normalization is adequate to receive the implant 720.

In particular, in the method illustrated in FIG. 11, the second normalizing step 708 may be followed by a second evaluating step 710 in which it is evaluated whether the second drill bit 100' can be fully inserted into the osteotomy in the second normalizing step 708. The second evaluating step 710 can be performed in substantially the same manner as detailed above for the first evaluating step 704.

If the second evaluating step 708 provides a positive result, an installing step 712 is performed.

In the installing step 712, the implant 720 is inserted into the osteotomy prepared with the drill bit 100', e.g., in the same manner as detailed above for the installing step 706. In the installing step 712, the implant 720 may be inserted into the jaw bone 730 under the application of an insertion torque in the range of about 35 to 70 Ncm (see FIG. 11).

If the second evaluating step 708 provides a negative result, a drilling step 714 is performed. The drilling step 714 can be performed using a drill bit that has a diameter larger than that of the pilot drill bit used in the pilot step 700. For example, the drill bit used in the drilling step 714 may have a diameter in the range of 3.4 to 3.9 mm. The drill bit used in the drilling step 714 may be a dense bone drill bit. The drilling step 714 can be performed using irrigation. The drill speed in the drilling step 714 can be about 800 rpm.

The drilling step 714 may be followed by another evaluating step (not shown in FIG. 11). This further evaluating step may be performed in substantially the same manner as detailed above for the first evaluating step 704.

After the drilling step 714, if the further evaluating step has provided a positive result, an installing step 716 may be performed. In the installing step 716, the implant 720 is inserted into the osteotomy prepared in the drilling step 714, e.g., in the same manner as detailed above for the installing step 706. In the installing step 716, the implant 720 may be inserted into the jaw bone 730 under the application of an insertion torque in the range of about 35 to 70 Ncm (see FIG. 11).

In the first and second normalizing steps 702, 708 detailed above, the threshold of the torque applied to the first drill bit 100 and the second drill bit 100', respectively, is chosen such that it is smaller than the torque threshold of the implant 720.

The implant 620 used in the above mentioned methods can be an implant as described in the International Patent Application PCT/EP2017/051953 entitled "Dental Implant, Insertion Tool for Dental Implant and Combination of Dental Implant and Insertion Tool", and filed on the same day as the present application by the Applicant, Nobel Biocare Services AG, the entirety of this application is hereby expressly incorporated by reference herein in particular the embodiments of FIGS. 1,2,10-12, 13-15, 20 and 21, 34 and 35 and related paragraphs of said application are expressly incorporated by reference herein. Said implant can be a dental implant, comprising: a core body having an apical end, a coronal end, and an outer surface extending along a longitudinal direction between said apical end and said coronal end; and at least one thread extending outwardly from said core body, wherein said core body comprises
    a first core shaped zone, in which first core shaped zone the cross-section of said core body has a number of main directions in which the radius measuring the distance between the center of the cross section and its outer contour takes a relative maximum value and thus a higher value than in neighboring orientations, a core circular zone, in which core circular zone the cross-section of said core body is basically circularly shaped, and a core transition zone positioned between said core shaped zone and said core circular zone, in which core transition zone the geometry of the cross-section of said core body, as a function of a parameter characteristic for a coordinate in said longitudinal direction, changes continuously from a basically circular shape next to said core circular zone to a shape in which the cross-section of said core body corresponds to the shape of the cross section in said core shaped zone.

Said implant can also have a second core shaped zone, in which second core shaped zone the cross-section of said core body has a number of main directions in which the radius measuring the distance between the center of the cross section and its outer contour takes a relative maximum value and thus a higher value than in neighbouring orientations, and wherein in said first core shaped zone a core eccentricity parameter defined as the ratio of the maximum radius of the cross section of said core body to its minimum radius is larger than in said second core shaped zone.

Such an implant can also comprise at least one thread extending outwardly from said core body, said thread defining a thread outer volume, wherein said thread comprises a first thread shaped zone, in which thread shaped zone the outer cross-section of said thread outer volume has a number of main directions in which the radius measuring the distance between the center of the cross section and its outer contour takes a relative maximum value and thus a higher value than in neighbouring orientations, a thread circular zone, preferably next to said apical end, in which thread circular zone the outer cross-section of said thread outer volume is basically circularly shaped, and a thread transition zone positioned between said thread shaped zone and said thread circular zone, in which thread transition zone the geometry of the outer cross-section of said thread outer volume, as a function of a parameter characteristic for a coordinate in said longitudinal direction, changes continuously from a basically circular shape next to said thread circular zone to a shape in which the outer cross-section of said thread outer volume corresponds to the shape of the outer cross section in said thread shaped zone.

The implant can also comprise a second thread shaped zone in which second thread shaped zone the outer cross-section of said thread outer volume has a number of main directions in which the radius measuring the distance between the center of the cross section and its outer contour takes a relative maximum value and thus a higher value than in neighboring orientations, wherein in said first thread shaped zone a core eccentricity parameter defined as the ratio of the maximum radius of the outer cross section of said thread outer volume to its minimum radius is larger than in said second core shaped zone.

Such an implant can also have a number of cutting flutes provided at least in said transition zone.

The dental implant, in particular for insertion into bone tissue of a patient, can also comprise:

a core body having an apical end, a coronal end, and an outer surface extending along a longitudinal direction between said apical end and said coronal end;

at least one thread extending outwardly from said core body, and a characteristic implant volume defined by said core body or by the thread outer volume as defined by said thread, in which for each value of a parameter characteristic for a coordinate in the implant's longitudinal direction the cross section of said characteristic implant volume is characterized by an eccentricity parameter defined as the ratio of the maximum distance of the contour of this cross section from its center to the minimum distance of the contour of this cross section from its center;

wherein said characteristic volume comprises at least one coronal zone in which said eccentricity parameter has a maximum, preferably a constant, value, said coronal zone extending along the implant's longitudinal axis over a coronal zone length of at least 10% of the total length of the implant;

at least one apical zone in which said eccentricity parameter has a minimum, preferably a constant, value, said apical zone extending along the implant's longitudinal axis over an apical zone length of at least 30% of the total length of the implant, and at least one transition zone positioned between said coronal zone and said apical zone in which said eccentricity parameter, as a function of a parameter characteristic for a coordinate in said longitudinal direction, changes continuously, preferably in a linear manner, from a minimum value next to said apical zone to a maximum value next to said coronal zone, said transition zone extending along the implant's longitudinal axis over a transition zone length of at least 10% of the total length of the implant.

Such a "non round implant" continues, during it insertion in the jawbone, the bone normalization initiated by a drill bit as above described.

According to another aspect the invention also concerns a kit of parts comprising and a drill bit as above defined and an implant, and in particular an implant as above defined.

It should be appreciated that certain embodiments and methods described above are in the context of dental surgery and forming a hole in a patient's jawbone to receive a dental implant; however, it should be appreciated that certain features and aspects of the embodiments described herein can also find utility in other surgical applications. For example, certain features and aspects of the embodiments described herein may be used in a drill configured to form a hole in another portion of the body (e.g., bones of the leg, spine, and/or arm) and/or a hole configured to receive a different type of device (e.g., a rod, a spacer, etc.)

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. A drill bit comprising:
   an apical end, a coronal end, and a longitudinal axis extending between the apical end and the coronal end;
   a drill bit core circumferentially surrounding the longitudinal axis and having at least a portion with a non-round profile when viewed in a plane perpendicular to the longitudinal axis, the portion with a non-round profile forming a plurality of lobes, each of the plurality of lobes forming at least one first compression zone, the drill bit core having a maximum radii at each of the plurality of lobes, wherein the drill bit core comprises a no-cutting zone at the maximum radii at each of the plurality of lobes;
   a plurality of flutes, each of the plurality of flutes corresponding with one of the plurality of lobes, each of the plurality of flutes positioned on a circumference of the drill bit core and at a circumferential distance away from the maximum radii of a corresponding one of the plurality of lobes, wherein each of the plurality of flutes comprises a first cutting edge formed on the drill bit core and positioned inwardly from the maximum radii of the corresponding one of the plurality of lobes of the drill bit core;
   a cutting zone extending inwardly from at least one of the cutting edges, wherein a position of the at least one cutting edge allows a hard bone to be positioned within the cutting zone and allows a soft bone to be positioned within the no-cutting zone, in use; and
   a guide thread which extends radially outward from the drill bit core.

2. The drill bit of claim 1 wherein each cutting edge of the plurality of flutes is disposed within the at least one compression zone of the corresponding one of the plurality of lobes.

3. The drill bit of claim 1 wherein the drill bit core tapers toward the apical end.

4. The drill bit of claim 1 wherein the maximum radii of at least one of the plurality of lobes circumferentially shifts about the longitudinal axis as the drill bit core extends toward the apical end.

5. The drill bit of claim 1 wherein the non-round profile forming the plurality of lobes is tri-lobed.

6. The drill bit of claim 1 wherein each of the plurality of flutes wraps circumferentially around the longitudinal axis as each of the plurality of flutes extends between the apical end and the coronal end of the drill bit.

7. The drill bit of claim 1 wherein the first cutting edge is a first radial distance from the longitudinal axis and the maximum radii of the drill bit core is a second radial distance from the longitudinal axis, the no-cutting zone defined as a difference between the second radial distance and the first radial distance.

8. The drill bit of claim 7, wherein the no-cutting zone remains constant between the apical and coronal ends of the drill bit.

9. A kit of parts comprising a drill bit of claim 1 and an implant.

10. The kit of parts of claim 9 wherein the implant comprises a thread, the guide thread of the drill bit differs from the thread of the implant in pitch and/or height and/or width.

11. A drill bit comprising:
    an apical end, a coronal end, and a longitudinal axis extending between the apical end and the coronal end;
    a drill bit core circumferentially surrounding the longitudinal axis and having at least a portion with a non-round profile when viewed in a plane perpendicular to the longitudinal axis, the portion with a non-round profile forming at least one compression zone;

a cutting edge disposed within the at least one compression zone of the drill bit core, wherein the cutting edge is a first radial distance from the longitudinal axis and a maximum outer dimension of the drill bit core is a second radial distance from the longitudinal axis, the second radial distance being larger than the first radial distance, wherein the drill bit core comprises a no-cutting zone at the maximum outer dimension, and wherein the no-cutting zone at the maximum outer dimension spirally wraps circumferentially around the longitudinal axis as the no-cutting zone at the maximum outer dimension extends between the apical portion and the coronal portion of the drill bit such that the maximum outer dimension shifts circumferentially along the length of the drill bit;

a cutting zone extending inwardly from the cutting edge, wherein a position of the cutting edge allows a hard bone to be positioned within the cutting zone and allows a soft bone to be positioned within the no-cutting zone, in use; and a guide thread which extends radially outward from the drill bit core.

12. The drill bit of claim 11, wherein the drill bit core further comprises a cutting flute, wherein the cutting flute comprises the cutting edge.

13. The drill bit of claim 12 wherein the cutting flute wraps circumferentially around the longitudinal axis as the cutting flute extends between the apical portion and the coronal portion of the drill bit.

14. A kit of parts comprising a drill bit of claim 11 and a dental implant.

15. The kit of parts of claim 14 wherein the dental implant comprises a thread, the guide thread of the drill bit differs from the thread of the dental implant in pitch and/or height and/or width.

16. The drill bit of claim 11 wherein the non-round profile forming the plurality of lobes is tri-lobed.

* * * * *

UNITED STATES PATENT AND TRADEMARK OFFICE
CERTIFICATE OF CORRECTION

| | | |
|---|---|---|
| PATENT NO. | : 11,045,287 B2 | Page 1 of 1 |
| APPLICATION NO. | : 16/073281 | |
| DATED | : June 29, 2021 | |
| INVENTOR(S) | : Edmund Burke | |

It is certified that error appears in the above-identified patent and that said Letters Patent is hereby corrected as shown below:

On the Title Page

On page 2, in Column 2, item (56), Other Publications, Lines 5-6, delete "sds.brocureEN.pdf;." and insert -- sds/brochureEN.pdf; --.

In the Claims

In Column 20, Line 10, Claim 1, delete "one first" and insert -- one --.

In Column 20, Line 21, Claim 1, delete "a first" and insert -- a --.

In Column 20, Line 48, Claim 7, delete "the first" and insert -- the --.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*